United States Patent
Farrand et al.

(10) Patent No.: US 6,849,203 B2
(45) Date of Patent: Feb. 1, 2005

(54) PHOTOISOMERIZABLE COMPOUNDS

(75) Inventors: Louise Diane Farrand, Davyhulme (GB); Christopher Worrall, Northwich (GB); Owain Llyr Parri, Poole (GB)

(73) Assignee: Merck Patent Gesellschaft Mit Beschraenkter Haftung, Darmstadt (DE)

( * ) Notice: Subject to any disclaimer, the term of this patent is extended or adjusted under 35 U.S.C. 154(b) by 180 days.

(21) Appl. No.: 10/115,940

(22) Filed: Apr. 5, 2002

(65) Prior Publication Data

US 2002/0187282 A1 Dec. 12, 2002

(30) Foreign Application Priority Data

Apr. 6, 2001 (EP) .............................................. 01108720

(51) Int. Cl.[7] .............................................. C09K 19/52
(52) U.S. Cl. ............................. 252/299.01; 252/299.61; 252/299.62; 252/299.64; 252/299.67; 428/1.1; 428/1.31; 540/467; 540/482; 540/546; 540/604; 540/611; 546/183; 546/290; 549/9; 549/28; 549/466; 549/468; 549/469; 549/477; 548/484
(58) Field of Search ........................ 252/299.01, 299.6, 252/299.61, 299.62, 299.63, 299.64, 299.65; 540/2, 106, 467, 482, 546, 604, 611; 546/1, 26, 183, 290; 548/400, 416, 484; 549/1, 6, 7, 9, 13, 29, 32, 200, 28, 346, 348, 429, 466, 468, 469, 477

(56) References Cited

FOREIGN PATENT DOCUMENTS

| JP | 02409253 | 8/1992 |
|---|---|---|
| JP | 4233520 A1 | 8/1992 |
| WO | WO 99/04789 A1 | 2/1999 |

OTHER PUBLICATIONS

T. Yamaguchi; T. Seki; T. Takashi; K. Ichimura "Photochromism of Hemithioindigo Derivatives I. Preparation and Photochromic Properties in Organic Solvents", The Bulletin of the Chemical Society of Japan, 65, 649–656 (1992).*

B.A. Brady; J. A. Kennedy; W.I. O'Sullivan "The Configuration of Aurones", Tetrahedron, 29, 359–362 (1973).*

A. Levai; C. Nemes; T. Patonay "Synthesis of New Z–3–Arylidenechromanones by the Photoisomerization of (E)–3–Arylidenechromanones", Heterocyclic Communications, 5(5) 441–444 (1999).*

A Riahi; C. Thorey; F. Henin; J. Muzart "2–Alkylidene–1–tetralones from Aldol Condensations", Synthetic Communications, 28(23), 4339–4344 (1998).*

G. Toth; J. Halasz; A. Levai; C. Nemes; T. Patonay "UV–induced Isomerization and Ring Transformation of (E)–3–arylidene–1–thiochromanones and –1–thioflavanones", Journal of the CHemical Society, Perkins Trans. 2, 547–550 (1996).*

Yamaguchi et al., "Photochromism of hemithioindigo derivatives. I. Preparation and photochromic properties in organic solvents," Bulletin of the Chemical Society of Japan, vol. 65, No. 3, 1992, pp. 649–656, XP002250487.

Seki et al., "Photochromism of hemithioindigo derivatives. II. Photochromic behaviors in bilayer membranes and related systems," Bulletin of the Chemical Society of Japan, vol. 65, No. 3, 1992, pp. 657–663, XP002250488.

Makoto, "Nonlinear optical material containing benzalindanone compound," Chemical Abstracts, vol. 118, No. 6, (Feb. 8, 1993), abstract No. 48951.

Search Report for EP 02 005204, completed Aug. 7, 2003.

* cited by examiner

Primary Examiner—Shean C. Wu
Assistant Examiner—Jennifer R. Sadula
(74) Attorney, Agent, or Firm—Millen White Zelano & Braninan, P.C.

(57) ABSTRACT

The invention relates to photoisomerizable compounds of formula I

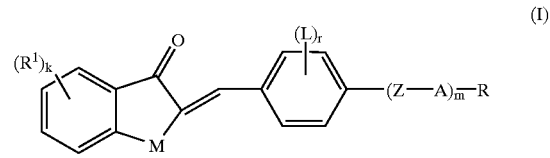

wherein A, Z, L, R, $R^1$, k, m and r are defined herein.

42 Claims, No Drawings

PHOTOISOMERIZABLE COMPOUNDS

The invention relates to novel photoisomerizable compounds, to liquid crystalline mixtures and polymers containing them, and to the use of the novel compounds such as formula I, liquid crystalline mixtures and the polymers in optical and electrooptical devices like liquid crystal displays or projection systems, patterned films and optical elements like polarizers, retardation films, compensators, color filters, holographic elements or polarization beam splitters, as sensitizers, for photoswitching, in anisotropic membranes for the permeation of gases or fluids, adhesives, synthetic resins with anisotropic mechanical properties, cosmetic or pharmaceutical compositions, UV absorbers and sunscreens, diagnostics or liquid crystal pigments, for decorative and security applications, in nonlinear optics, optical information storage or as dopants.

In prior art photoisomerizable mesogenic molecules are reported which change their shape on photo-irradiation. When irradiated e.g. with UV light, they show E-Z or cis-trans isomerization.

Photoisomerizable compounds can be used in liquid crystal host mixtures as switchable materials or for changing the birefringence of the host mixture. Polymerizable liquid crystal mixtures comprising photoisomerizable compounds can be used for the preparation of patterned anisotropic polymer films. The photoisomerizable compounds and the liquid crystal mixtures and polymer films prepared thereof can be used for example as optical element like color filters or polarization beam splitters, in information storage device, anisotropic membranes for the permeation of gases, or in photoswitching devices.

Compounds of the Formula

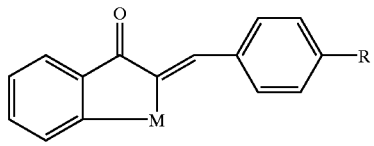

wherein R is an organic residue and M is short alkylene or heteroalkylene, undergo EZ photoisomerisation when irradiated with UV light, thus changing from the E conformation to the Z conformation as shown below.

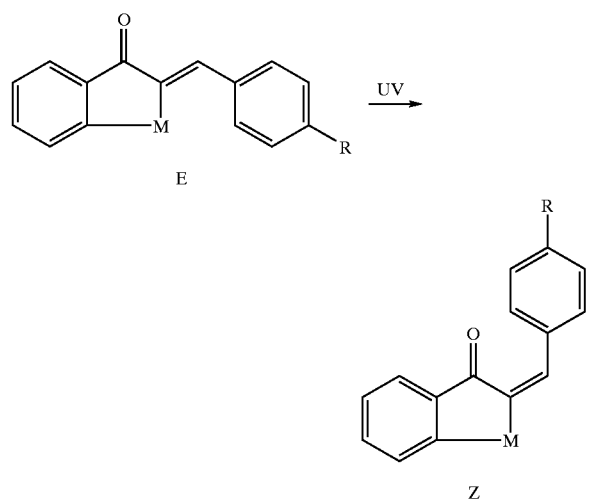

The inventors found that when these compounds are added to a liquid crystal host mixture, the EZ photoisomerisation disrupts the parallel stacking of the mesogens in the liquid crystal mixture, leading to a change of the birefringence. If so desired, the above compounds can even be used to cause a transition from the liquid crystal phase to the isotropic phase.

Furthermore the inventors found that compounds of the above formula wherein R is a mesogenic group and/or a polymerizable group are particular useful for the preparation of liquid crystal mixtures for photoswitching or the preparation of patterned polymer films. Compounds of the above formula that show mesogenic phase behaviour are particularly useful, as they do not negatively affect the liquid crystalline phase of the host mixture.

JP 04-233520 A discloses a nonlinear optical material comprising indanone derivatives of the following formula

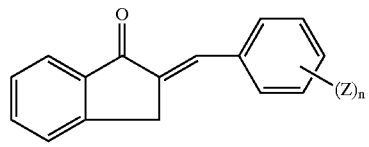

wherein n is 1 to 5 and Z is $C_{1-10}$-alkyl, $C_{1-10}$-alkoxy, aryl, aralkyl, aralkyloxy, haloalkyl, Br or Cl. The indanone derivatives are said to generate a large dipole moment by charge transfer in an excited state to give high super polarizibility.

U.S. Pat. Nos. 5,112,721, 4,162,162 and EP 0 483 648 disclose indanone derivatives of the formula

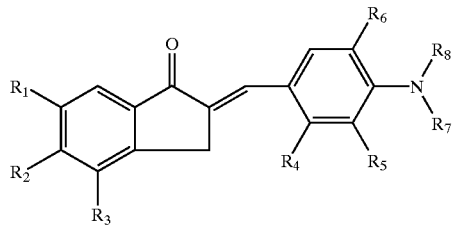

wherein $R_1$ to $R_8$ are hydrogen or alkyl, for use as coinitiators sensitizers in photopolymerizable compositions.

However, the above prior art documents do not give a hint to mesogenic or polymerizable compounds according to the present invention, or to their use as photoisomerizable compounds for the preparation of patterned polymer films.

The invention has the aim of providing new compounds, in particular polymerizable and/or mesogenic compounds, which are suitable as photoisomerizable compounds and for other uses, are easy to synthesize in a large range of derivatives, preferably show broad liquid crystalline phases with high clearing points and, when added to a liquid crystalline host mixture, do not greatly affect the properties of the host mixture. Another aim of the invention is to provide liquid crystal mixtures comprising photoisomerizable compounds.

It has been found that the above aims can be achieved by providing mixtures and compounds as claimed in the present invention.

The terms 'liquid crystalline or mesogenic material' or 'liquid crystalline or mesogenic compound' should denote materials or compounds comprising one or more rod-shaped, lath-shaped or disk-shaped mesogenic groups, i.e. groups with the ability to induce liquid crystal phase behaviour. Rod-shaped and lath-shaped mesogenic groups are especially preferred. The compounds or materials comprising mesogenic groups do not necessarily have to exhibit a liquid crystal phase themselves. It is also possible that they show liquid crystal phase behaviour only in mixtures with other compounds, or when the mesogenic compounds or materials, or the mixtures thereof, are polymerized.

The term 'reactive mesogen' means a polymerizable mesogenic compound.

For the sake of simplicity, the term 'liquid crystal material' is used hereinafter for both liquid crystal materials and mesogenic materials.

The term 'film' includes self-supporting, i.e. freestanding, films that show more or less pronounced mechanical stability and flexibility, as well as coatings or layers on a supporting substrate or between two substrates.

The term 'photoisomerizable group' means a group that shows isomerization, for example cis-trans or E-Z isomerization, imparting a change in shape upon photoirradiation with a suitable wavelength, preferably in the range from 250 to 400 nm, very preferably from 300 to 400 nm.

SUMMARY OF THE INVENTION

One feature of the invention is a compound of formula I

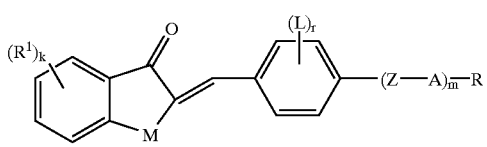

wherein

M is $(CH_2)_i$, wherein one $CH_2$ group may also be replaced by $NR^0$, O or S, is 1, 2, 3 or 4, $R^0$ is H or alkyl with 1 to 4 C atoms, L is halogen, CN, SCN, $NO_2$, $SF_5$ or an alkyl, alkoxy, alkylcarbonyl or alkoxycarbonyl group with 1 to 4 C atoms, wherein one or more H atoms may be substituted with F or Cl, r is 0, 1, 2, 3 or 4, $R^1$ is in each case independently OH, O—B, $OCH_2B$ or has one of the meanings of R given below, k is 0, 1, 2, 3 or 4, A and B are independently of each other an aromatic or alicyclic group with 4 to 12 C-atoms, Z is in each case independently —O—, —S—, —CO—, —COO—, —OCO—, —CO—$NR^0$—, —$NR^0$—CO—, —$CH_2CH_2$—, —$CF_2CF_2$—, —$CH_2CF_2$—, —$OCH_2$—, —$CH_2O$—, —$SCH_2$—, —$CH_2S$—, —$CF_2O$—, —$OCF_2$—, —CH=CH—, —CF=CF—, —CH=CF—, —$(CH_2)_4$—, —CH=CH—COO—, —OCO—CH=CH—, —OOC—$CHR^{oo}$—OOC—, —COO—$CHR^{oo}$—COO—, —C≡C— or a single bond, $R^{oo}$ is straight chain or branched alkyl or alkoxy with 1 to 8 C atoms or phenyl that is optionally mono- or polysubstituted by L, m is 0, 1 or 2, R is H, halogen, $NO_2$, CN, SCN, $SF_5$, straight chain, branched or cyclic alkyl with 1 to 25 C atoms wherein one or more $CH_2$ groups can also be replaced by —O—, —S—, —CO—, —$NR^0$—, —CH=CH—, —C≡C— in such a manner that O and/or S atoms are not linked directly to one another, and wherein one or more H-atoms can also be replaced by F, Cl or phenyl that is optionally mono- or polysubstituted by L, or denotes $P-(Sp-X)_n$—, P is a polymerizable group, Sp is a spacer group with 1 to 20 C atoms, X has one of the meanings of Z, and n is 0 or 1.

Another feature of the invention is a liquid crystalline mixture comprising one or more compounds of formula I.

Another feature of the present invention is a polymerizable liquid crystalline mixture comprising at least two compounds, at least one of which is a compound of formula I and at least one of which is a polymerizable compound.

Another feature of the invention is a linear or crosslinked anisotropic polymer obtainable by polymerizing a polymerizable liquid crystalline mixture comprising one or more compounds of formula I.

Another feature of the invention is the use of a compound of formula I, mixture or polymer as described above in optical and electrooptical devices like liquid crystal displays or projection systems, such as STN, TN, AMD-TN, temperature compensation, ferroelectric, guest-host, phase change or surface stabilized or polymer stabilized cholesteric texture (SSCT, PSCT) displays, in optical elements, like reflective polarizers, retardation films, compensators, color filters, polarization beam splitters or holographic elements, especially in films with patterned optical properties, in adhesives, synthetic resins with anisotropic mechanical properties like for example anisotropic membranes for the permeation of gases or fluids, cosmetic and pharmaceutical compositions like for example UV absorbers, UV filters or sunscreens, as sensitizers, in diagnostics, liquid crystal pigments, for decorative and security applications, especially in security markings that are applied to items or documents of value for easy identification or prevention of falsification, in nonlinear optics, optical recording or information storage, or as dopants.

Another feature of the invention is an anisotropic polymer film comprising a compound of formula I.

Another feature of the invention is an anisotropic polymer film with patterned optical properties comprising a compound of formula I.

Inventive compounds are preferred that are mesogenic or liquid crystalline, i.e. they can induce or enhance mesophase behaviour for example in a mixture with other compounds or exhibit one or more mesophases themselves. It is also possible that the inventive compounds show mesophase behaviour only in mixtures with other compounds, or, in case of polymerizable compounds, when being (co) polymerized. Mesogenic inventive compounds are especially preferred.

The inventive compounds have several advantages they can easily be synthesized, also on large scale of several hundred grams, with a broad range of derivatives using standard methods that are known from the literature, the starting materials can be obtained commercially or synthesized cheaply using methods known from the literature they exhibit a good solubility in liquid crystalline mixtures, they exhibit mesophase behaviour and in the ideal case broad liquid crystalline phases.

Photolysis of the compounds of formula I with e.g. UV light of 360 nm has the effect of isomerising the double bond of the cycloalkanone group from E to Z, thus completely changing the shape of the molecule and hence the physical molecular properties. The inventive compounds of formula I can be mixed with other polymerizable mesogenic compounds to give a liquid crystalline mixture. If such a liquid crystalline mixture, for example a nematic mixture is aligned on a surface and then photolysed with e.g. UV light of 360 nm, the light changes the shape of the isomerizable dopant—this in turn disrupts the parallel alignment of the mixture, and this has an overall effect of reducing the birefringence of the mixture.

If irradiation is carried out through a mask towards a liquid crystalline mixture doped with the photoisomerizable compound, and the resulting film is viewed between crossed polarisers, the change of birefringence shows a lower retardation in areas of higher UV transmission.

The compounds of formula I are thus useful e.g. for forming optical films with novel architectures.

Particularly preferred are compounds of formula I wherein M is $CH_2$, $NR^0$, O, S, $(CH_2)_2$, $NR^0$—$CH_2$, O—$CH_2$ or S—$CH_2$, very preferably $CH_2$ or $(CH_2)_2$. $R^0$ is preferably H or $CH_3$.

Further preferred are compounds of formula I wherein

A is in each case independently 1,4-phenylene in which, in addition, one or more CH groups may be replaced by N, 1,4-cyclohexylene in which, in addition, one or two non-adjacent $CH_2$ groups may be replaced by O and/or S, 1,3-dioxolane-4,5-diyl, 1,4-cyclohexenylene, piperidine-1,4-diyl, pyrrolidine-2,4-diyl, 1,4-bicyclo-(2,2,2)-octylene, naphthalene-2,6-diyl, decahydro-naphthalene-2,6-diyl, 1,2,3,4-tetrahydronaphthalene-2,6-diyl or indane-2,5-diyl, it being possible for all these groups to be unsubstituted, mono- or polysubstituted with L as defined in formula I.

Further preferred are compounds of formula I wherein
one or more of R and $R^1$ denote P-$(Sp-X)_n$,
R and/or $R^1$ are straight chain or branched, very preferably straight chain alkyl or alkoxy with 1 to 12 C atoms,
m is 1 or 2, very preferably 1,
k is 0 or 1,
k is 1, 2, 3 or 4 and at least one $R^1$ is different from H,
n is 1,
M is $CH_2$ or $OCH_2$ and at least one of R and $R^1$ is P-$(Sp-X)_n$,
M is $CH_2$ or $OCH_2$ and m is 1, preferably with Z not being O or a single bond,
M is $CH_2$ or $OCH_2$ and k is 1, 2, 3 or 4.

Further preferred are compounds of formula I comprising one or two, very preferably two polymerizable groups.

The group B in formula I is preferably a monocyclic or bicyclic aromatic or alicyclic group having preferably 6 to 10 C atoms. Especially preferably B has one of the preferred meanings of A given above.

Particularly preferred are compounds of formula I wherein the group $(Z-A)_m$ is selected from the group of formulae listed below. For reasons of simplicity, Phe in these formulae is 1,4-phenylene that may also be substituted with 1 to 4 groups L as defined in formula II, Cyc is 1,4-cyclohexylene and Z has one of the meanings of formula II. The list is comprising the following subformulae as well as their mirror images

| | |
|---|---|
| -Phe- | II-1 |
| -Cyc- | II-2 |
| -Phe-Z-Phe- | II-3 |
| -Phe-Z-Cyc- | II-4 |
| -Cyc-Z-Cyc- | II-5 |

Z is preferably —COO—, —OCO—, —$CH_2CH_2$— or a single bond.

A particularly preferred embodiment relates to compounds wherein at least one group Z is a chiral group OOC—$CHR^{00}$—OOC or COO—$CHR^{00}$—COO. $R^{00}$ in these groups is preferably phenyl or straight-chain or branched alkyl with 2 to 5 C atoms\, very preferably phenyl or 2-methylpropyl.

Very preferably the group

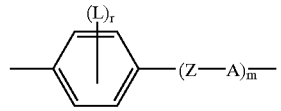

in formula I is selected from the following formulae

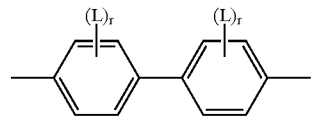  IIa

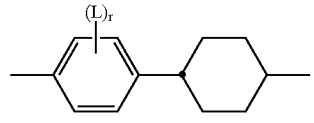  IIb

IIc

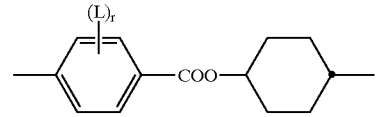  IId

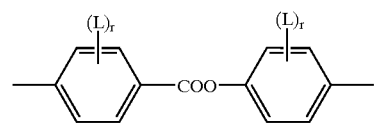  IIe

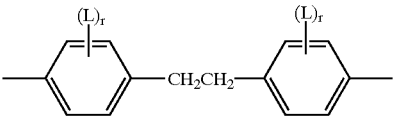  IIf

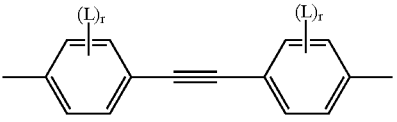  IIg

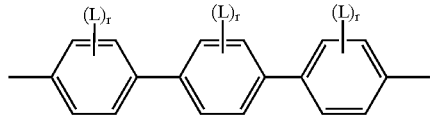  IIh

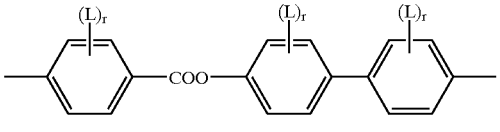  IIi

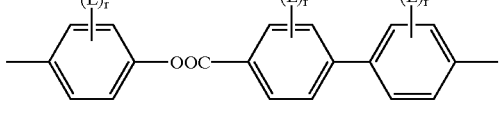  IIk

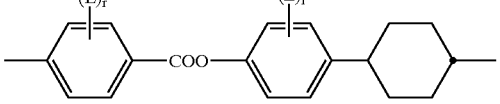

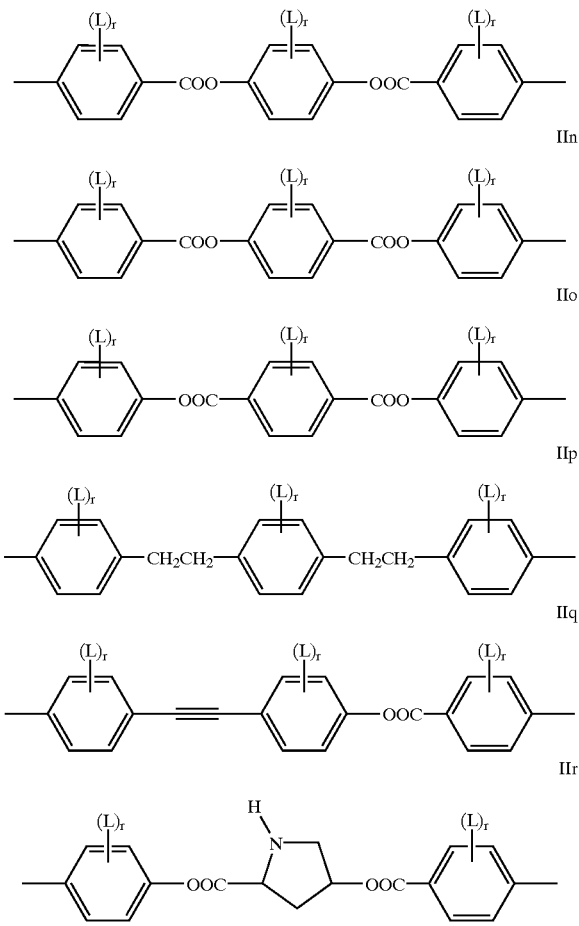

wherein L and r have the above meanings, and r is preferably 0, 1 or 2.

The group

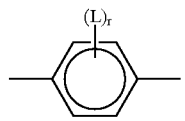

in these preferred formulae is very preferably denoting

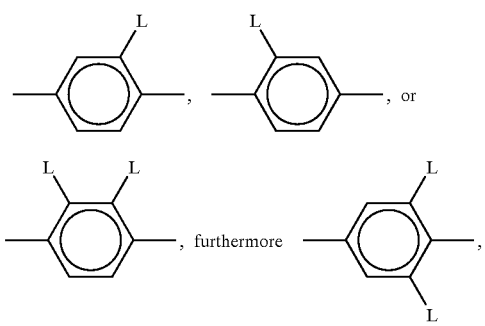

with L having each independently one of the meanings given above.

Particularly preferred are the subformulae IId, IIg, IIh, IIi, IIm, IIn and IIo, in particular the subformula IId.

L is preferably F, Cl, CN, $NO_2$, $CH_3$, $C_2H_5$, $OCH_3$, $OC_2H_5$, $COCH_3$, $COC_2H_5$, $COOCH_3$, $COOC_2H_5$, $CF_3$, $OCF_3$, $OCHF_2$ or $OC_2F_5$, in particular F, Cl, CN, $CH_3$, $C_2H_5$, $OCH_3$, $COCH_3$, $CF_3$ or $OCF_3$, most preferably F, Cl, $CH_3$, $OCH_3$ or $OCF_3$.

Particularly preferred compounds of formula I are those of the following subformulae

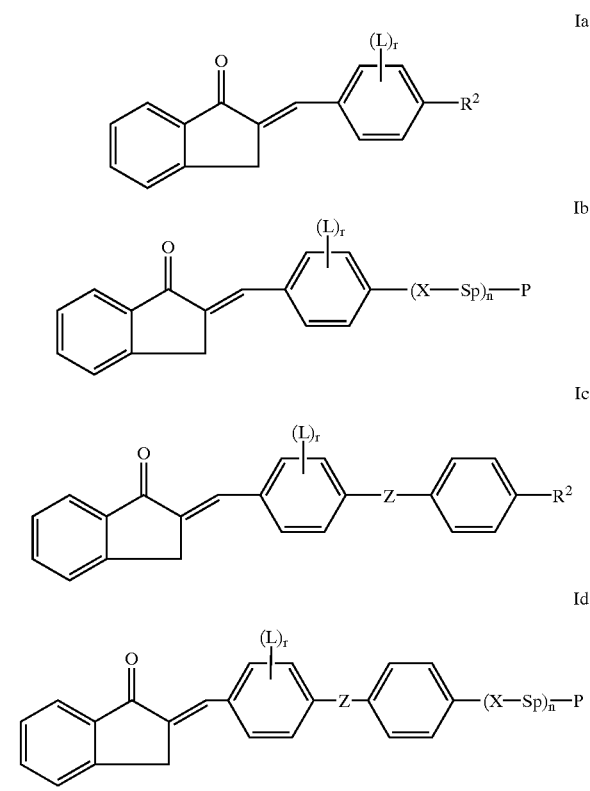

wherein Z, P, Sp, X, L, n and r are as defined in formula I and $R^2$ is H, halogen, $NO_2$, CN, SCN, $SF_5$, straight chain, branched or cyclic alkyl with 1 to 25 C atoms wherein one or more $CH_2$ groups can also be replaced by —O—, —S—, —CO—, $—NR^o—$, —CH=CH—, —C≡C— in such a manner that O and/or S atoms are not linked directly to one another, and wherein one or more H-atoms can also be replaced by F or Cl.

Particularly preferred are compounds of formula Ia to Id wherein r is 0. Further preferred are compounds of formula Ib and Id wherein Z is COO, OCO, $CH_2CH_2$ or a single bond.

If R, $R^1$ or $R^2$ is an alkyl or alkoxy radical, i.e. where the terminal $CH_2$ group is replaced by —O—, this may be straight-chain or branched. It is preferably straight-chain, has 2, 3, 4, 5, 6, 7 or 8 carbon atoms and accordingly is preferably ethyl, propyl, butyl, pentyl, hexyl, heptyl, octyl, ethoxy, propoxy, butoxy, pentoxy, hexoxy, heptoxy, or octoxy, furthermore methyl, nonyl, decyl, undecyl, dodecyl, tridecyl, tetradecyl, pentadecyl, nonoxy, decoxy, undecoxy, dodecoxy, tridecoxy or tetradecoxy, for example.

Especially preferred is straight chain alkyl or alkoxy with 1 to 8 C atoms.

Oxaalkyl, i.e. where one $CH_2$ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

R, $R^1$ and $R^2$ can be a polar or an unpolar group.

In case of a polar group, it is preferably selected from CN, $NO_2$, halogen, $OCH_3$, SCN, $COR^8$, $COOR^8$ or a mono- oligo- or polyfluorinated alkyl or alkoxy group with 1 to 4 C atoms. $R^8$ is optionally fluorinated alkyl with 1 to 4, preferably 1 to 3 C atoms. Especially preferably polar groups are selected of F, Cl, CN, $NO_2$, $OCH_3$, $COCH_3$, $COC_2H_5$, $COOCH_3$, $COOC_2H_5$, $CF_3$, $C_2F_5$, $OCF_3$, $OCHF_2$, and $OC_2F_5$, in particular of F, Cl, CN, $OCH_3$ and $OCF_3$.

In case of an unpolar group, it is preferably alkyl with up to 15 C atoms or alkoxy with 2 to 15 C atoms.

R, $R^1$ and $R^2$ can be an achiral or a chiral group. In case of a chiral group, it is preferably selected according to formula IV:

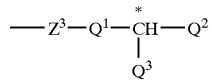

wherein $Z^3$ is —O—, —S—, —CO—, —COO—, —OCO—, —OCOO— or a single bond, $Q^1$ is an alkylene or alkylene-oxy group with 1 to 9 C atoms or a single bond, $Q^2$ is an alkyl or alkoxy group with 1 to 10 C atoms which may be unsubstituted, mono- or polysubstituted with halogen or CN, it being also possible for one or more non-adjacent $CH_2$ groups to be replaced, in each case independently from one another, by —C≡C—, —O—, —S—, —$NR^0$—, —CO—, —COO—, —OCO—, —OCO—O—, —S—CO— or —CO—S— in such a manner that oxygen atoms are not linked directly to one another, $Q^3$ is halogen, a cyano group, an alkyl or alkoxy group with 1 to 4 C atoms different from $Q^2$, or a phenyl group that may also be mono- or polysubstituted with L as defined in formula I.

In case $Q^1$ in formula IV is an alkylene-oxy group, the O atom is preferably adjacent to the chiral C atom.

Preferred chiral groups are 2-alkyl, 2-alkoxy, 2-carbonyl, 2-carbonyloxy, 2-oxycarbonyl, 2-methylalkyl, 2-methylalkoxy, 2-methylcarbonyl, 2-methylcarbonyloxy, 2-methyloxycarbonyl, 2-fluoroalkyl, 2-fluoroalkoxy, 2-(2-ethin)-alkyl, 2-(2-ethin)-alkoxy, 1,1,1-trifluoro-2-alkyl, 1,1, 1-trifluoro-2-alkoxy, 2-phenylalkyl, 2-phenylalkoxy, 2-phenylcarbonyl, 2-phenylcarbonyloxy and 2-phenyloxycarbonyl.

Particularly preferred chiral groups are 2-butyl (=1-methylpropyl), 2-methylbutyl, 2-methylpentyl, 3-methylpentyl, 2-ethylhexyl, 2-propylpentyl, in particular 2-methylbutyl, 2-methylbutoxy, 2-methylpentoxy, 3-methylpentoxy, 2-ethylhexoxy, 1-methylhexoxy, 2-octyloxy, 2-oxa-3-methylbutyl, 3-oxa-4-methylpentyl, 4-methylhexyl, 2-hexyl, 2-octyl, 2-nonyl, 2-decyl, 2-dodecyl, 6-methoxyoctoxy, 6-methyloctoxy, 6-methyloctanoyloxy, 5-methylheptyloxycarbonyl, 2-methylbutyryloxy, 3-methylvaleroyloxy, 4-methylhexanoyloxy, 2-chlorpropionyloxy, 2-chloro-3-methylbutyryloxy, 2-chloro-4-methylvaleryloxy, 2-chloro-3-methylvaleryloxy, 2-methyl-3-oxapentyl, 2-methyl-3-oxahexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy, 2-phenylbutyl, 2-phenylbutyloxy, 2-phenylpropylcarbonyl, 2-phenylpropylcarbonyloxy, for example. Very preferred are 2-hexyl, 2-octyl, 2-octyloxy, 1,1,1-trifluoro-2-hexyl, 1,1,1-trifluoro-2-octyl and 1,1,1-trifluoro-2-octyloxy, for example.

In addition, compounds of formula I containing an achiral branched group R or $R^3$ may occasionally be of importance, for example, due to a reduction in the tendency towards crystallization. Branched groups of this type generally do not contain more than one chain branch. Preferred achiral branched groups are isopropyl, isobutyl (=methylpropyl), isopentyl (=3-methylbutyl), isopropoxy, 2-methyl-propoxy and 3-methylbutoxy.

Another preferred embodiment of the present invention relates to compounds of formula I wherein R, $R^1$ or $R^2$ is denoting P-(Sp-X)$_n$.

$R^0$ in formula I is preferably H or $CH_3$, in particular H.

The polymerisable group P is preferably selected from $CH_2=CW^1—COO—$,

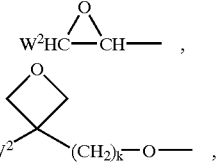

$CH_2=CW^2—O—$, $CH_3—CH=CH—O—$, $HO—CW^2W^3—$, $HS—CW^2W^3—$, $HW^2N—$, $HO—CW^2W^3—NH—$, $CH_2=CW^1—CO—NH—$, $CH_2=CH—(COO)_{k1}$-Phe-$(O)_{k2}$—, Phe-CH=CH—, HOOC—, OCN— and $W^4W^5W^6Si—$, with $W^1$ being H, Cl, CN, phenyl or alkyl with 1 to 5 C-atoms, in particular H, Cl or $CH_3$, $W^2$ and $W^3$ being independently of each other H or alkyl with 1 to 5 C-atoms, in particular methyl, ethyl or n-propyl, $W^4$, $W^5$ and $W^6$ being independently of each other Cl, oxaalkyl or oxacarbonylalkyl with 1 to 5 C-atoms, Phe being 1,4-phenylene and $k_1$ and $k_2$ being independently of each other 0 or 1.

P is particularly preferably an acrylate, methacrylate, vinyl, vinyloxy, epoxy, styrene or propenyl ether group, in particular an acrylate, methacrylate, vinyl or epoxy group.

As spacer group Sp in formula I all groups can be used that are known for this purpose to the skilled in the art. Sp is preferably a straight chain or branched alkylene group having 1 to 20 C atoms, in particular 1 to 12 C atoms, in which, in addition, one or more non-adjacent $CH_2$ groups may be replaced by —O—, —S—, —$NR^0$—, —CO—, —O—CO—, —S—CO—, —O—COO—, —CO—S—, —CO—O—, —CH(halogen)-, —CH(CN)—, —CH(OH)—, —$(CF_2)_x$—, —$(CD_2)_x$-, —CH=CH—, —CF=CF—, —CH=CF— or —C≡C—, with x being an integer from 1 to 12, and in which one or more H atoms may be replaced by halogen, CN or OH.

Typical spacer groups are for example —$(CH_2)_y$—, —$(CH_2CH_2O)_z$—$CH_2CH_2$—, —$CH_2CH_2$—S—$CH_2CH_2$— or —$CH_2CH_2$—NH—$CH_2CH_2$—, with y being an integer from 2 to 12 and p being an integer from 1 to 3.

Preferred spacer groups are ethylene, propylene, butylene, pentylene, hexylene, heptylene, octylene, nonylene, decylene, undecylene, dodecylene, octadecylene, ethyleneoxyethylene, methyleneoxybutylene, ethylene-thioethylene, ethylene-N-methyl-iminoethylene, 1-methylalkylene, ethenylene, propenylene and butenylene for example.

Especially preferred are inventive compounds of formula I wherein Sp is denoting alkylene or alkylene-oxy with 2 to 8 C atoms. Straight-chain groups are especially preferred.

In another preferred embodiment of the invention the compounds of formula I comprise at least one spacer group Sp that is a chiral group of formula V:

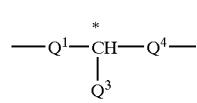

wherein
$Q^1$ and $Q^3$ have the meanings given in formula IV, and
$Q^4$ is an alkylene or alkylene-oxy group with 1 to 10 C atoms or a single bond, being different from $Q^1$.

In case $Q^1$ in formula V is an alkylene-oxy group, the O atom is preferably adjacent to the chiral C atom.

Throughout this text, halogen is preferably F or Cl.

The inventive compounds can be synthesized according to or in analogy to methods which are known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for said reactions. Use may also be made here of variants which are known per se, but are not mentioned here. Further methods for preparing the inventive compounds can be taken from the examples.

The inventive compounds can be used in a liquid crystal mixture for liquid crystal displays. Thus, another feature of the invention is a liquid crystalline mixture comprising at least one compound of formula I.

Many of the inventive compounds are characterized by a good solubility in liquid crystalline host mixtures, and can be added as dopants to liquid crystalline hosts in high amounts without significantly affecting the phase behaviour and electrooptical properties of the mixture. Undesired spontaneous crystallization at low temperatures is thereby reduced and the operating temperature range of the mixture can be broadened.

A liquid crystalline mixture according to the invention comprises preferably 0.1 to 30%, in particular 1 to 25% and very particularly preferably 2 to 15% by weight of compounds of formula I.

A liquid crystalline mixture according to the invention preferably comprises 1 to 3 chiral compounds of formula I.

In a preferred embodiment of the invention the liquid crystalline mixture is consisting of 2 to 25, preferably 3 to 15 compounds, at least one of which is a compound of formula I. The other compounds are preferably low molecular weight liquid crystalline compounds selected from nematic or nematogenic substances, for example from the known classes of the azoxybenzenes, benzylidene-anilines, biphenyls, terphenyls, phenyl or cyclohexyl benzoates, phenyl or cyclohexyl esters of cyclohehexanecarboxylic acid, phenyl or cyclohexyl esters of cyclohexylbenzoic acid, phenyl or cyclohexyl esters of cyclohexylcyclohexanecarboxylic acid, cyclohexylphenyl esters of benzoic acid, of cyclohexanecarboxylic acid and of cyclohexylcyclohexanecarboxylic acid, phenylcyclohexanes, cyclohexylbiphenyls, phenylcyclohexylcyclohexanes, cyclohexylcyclohexanes, cyclohexylcyclohexenes, cyclohexylcyclohexylcyclohexenes, 1,4-bis-cyclohexylbenzenes, 4,4'-bis-cyclohexylbiphenyls, phenyl- or cyclo-hexylpyrimidines, phenyl- or cyclohexylpyridines, phenyl- or cyclo-hexylpyridazines, phenyl- or cyclohexyldioxanes, phenyl- or cyclo-hexyl-1,3-dithianes, 1,2-diphenyl-ethanes, 1,2-dicyclohexylethanes, 1-phenyl-2-cyclohexylethanes, 1-cyclohexyl-2-(4-phenylcyclohexyl)-ethanes, 1-cyclohexyl-2-biphenyl-ethanes, 1-phenyl-2-cyclohexyl-phenylethanes, optionally halogenated stilbenes, benzyl phenyl ether, tolanes, substituted cinnamic acids and further classes of nematic or nematogenic substances. The 1,4-phenylene groups in these compounds may also be laterally mono- or difluorinated.

The liquid crystalline mixture of this preferred embodiment is based on the achiral compounds of this type.

The most important compounds that are posssible as components of these liquid crystalline mixtures can be characterized by the following formula

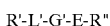

wherein L' and E, which may be identical or different, are in each case, independently from one another, a bivalent radical from the group formed by -Phe-, -Cyc-, -Phe-Phe-, -Phe-Cyc-, -Cyc-Cyc-, -Pyr-, -Dio-, —B-Phe- and —B-Cyc- and their mirror images, where Phe is unsubstituted or fluorine-substituted 1,4-phenylene, Cyc is trans-1,4-cyclohexylene or 1,4-cyclohexenylene, Pyr is pyrimidine-2,5-diyl or pyridine-2,5-diyl, Dio is 1,3-dioxane-2,5-diyl abd B is 2-(trans-1,4-cyclohexyl)ethyl, pyrimidine-2,5-diyl, pyridine-2,5-diyl or 1,3-dioxane-2,5-diyl.

G' in these compounds is selected from the following bivalent groups —CH=CH—, —N(O)N—, —CH=CY—, —CH=N(O)—, —C≡C—, —CH$_2$—CH$_2$—, —CO—O—, —CH$_2$—O—, —CO—S—, —CH$_2$—S—, —CH=N—, —COO-Phe-COO— or a single bond, with Y being halogen, preferably chlorine, or —CN.

R' and R" are, in each case, independently of one another, alkyl, alkenyl, alkoxy, alkenyloxy, alkanoyloxy, alkoxycarbonyl or alkoxycarbonyloxy with 1 to 18, preferably 3 to 12 C atoms, or alternatively one of R' and R" is F, CF$_3$, OCF$_3$, Cl, NCS or CN.

In most of these compounds R' and R" are, in each case, independently of each another, alkyl, alkenyl or alkoxy with different chain length, wherein the sum of C atoms in nematic media generally is between 2 and 9, preferably between 2 and 7.

Many of these compounds or mixtures thereof are commercially available. All of these compounds are either known or can be prepared by methods which are known per se, as described in the literature (for example in the standard works such as Houben-Weyl, Methoden der Organischen Chemie [Methods of Organic Chemistry], Georg-Thieme-Verlag, Stuttgart), to be precise under reaction conditions which are known and suitable for said reactions. Use may also be made here of variants which are known per se, but are not mentioned here.

A preferred use of the inventive compounds is the preparation of polymerizable liquid crystalline mixtures, anisotropic polymer gels and anisotropic polymer films, in particular oriented polymer films that exhibit a pattern of different regions with different orientation as describe above.

Patterned polymer films can be used for example as optical elements like color filters or polarization beam splitters, alignment layers, security markings or anisotropic membranes for the permeation of gases or fluids. Furthermore, the inventive polymers and polymer gels can eb used in optical information storage devices or nonlinear optics.

For the preparation of anisotropic polymer gels or oriented polymer films, the liquid crystalline mixture should comprise at least one polymerizable compound, preferably a polymerizable mesogenic compound.

Thus, another feature of the invention are polymerizable liquid crystalline mixtures comprising at least two compounds, at least one of which is a compound of formula I and at least one of which is a polymerizable compound. The polymerizable compound can be said at least one compound of formula I or an additional compound.

Examples of suitable polymerizable mesogenic compounds that can be used as co-components in the polymerizable mixture are disclosed for example in WO 93/22397; EP 0,261,712; DE 195,04,224; WO 95/22586 and WO 97/00600. The compounds disclosed in these documents, however, are to be regarded merely as examples that shall not limit the scope of this invention. Preferably the polymerizable mixture comprises at least one polymerizable mesogenic compound having one polymerizable functional group and at least one polymerizable mesogenic compound having two or more polymerizable functional groups.

Examples of especially useful mono- and direactive chiral and achiral polymerizable mesogenic compounds are shown in the following list of compounds, which should, however, be taken only as illustrative and is in no way intended to restrict, but instead to explain the present invention:

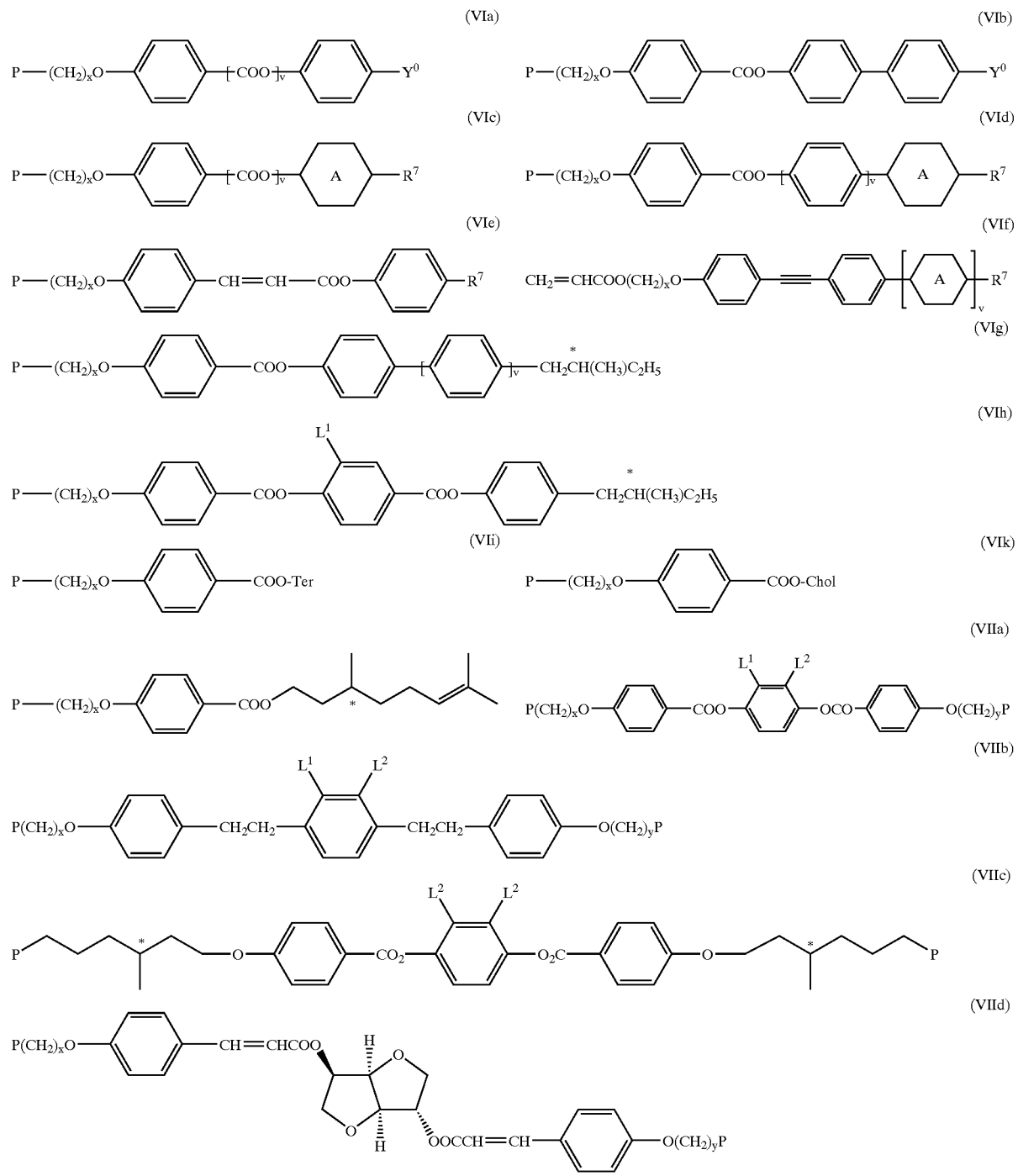

(VIIe)

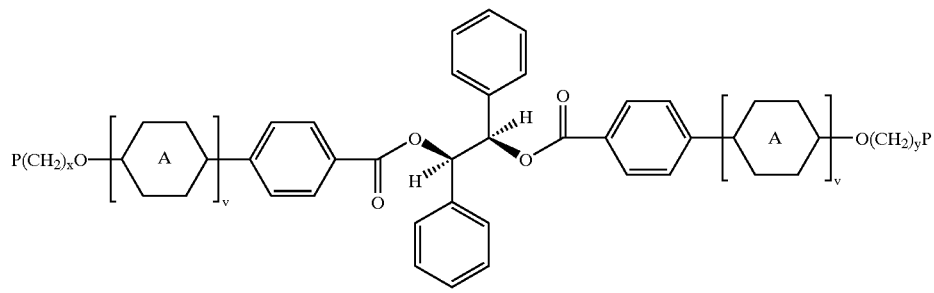

wherein, P has one of the meanings given above, x and y are identical or different integers from 1 to 12, A is 1,4-phenylene or 1,4-cyclohexylene, v is 0 or 1, $Y^0$ is a polar group, $R^7$ is an unpolar alkyl or alkoxy group, Ter is a terpenoid radical like e.g. menthyl, Chol is a cholesteryl group, and $L^1$ and $L^2$ are each independently H, F, Cl, CN, OH, $NO_2$ or an optionally halogenated alkyl, alkoxy or carbonyl group with 1 to 7 C atoms.

The polar group $Y^0$ is preferably CN, $NO_2$, halogen, $OCH_3$, OCN, SCN, $COR^8$, $COOR^8$ or a mono- oligo- or polyfluorinated alkyl or alkoxy group with 1 to 4 C atoms. $R^8$ is optionally fluorinated alkyl with 1 to 4, preferably 1 to 3 C atoms. Especially preferably the polar group $Y^0$ is selected of F, Cl, CN, $NO_2$, $OCH_3$, $COCH_3$, $COC_2H_5$, $COOCH_3$, $COOC_2H_5$, $CF_3$, $C_2F_5$, $OCF_3$, $OCHF_2$, and $OC_2F_5$, in particular F, Cl, CN, $OCH_3$ and $OCF_3$.

The unpolar group $R^7$ is preferably an alkyl group with 1 or more, preferably 1 to 15 C atoms or an alkoxy group with 2 or more, preferably 2 to 15 C atoms.

The mono- and difunctional polymerizable mesogenic compounds of above formulae VI and VII can be prepared by methods which are known per se and which are described in the documents cited above and, for example, in standard works of organic chemistry such as, for example, Houben-Weyl, Methoden der organischen Chemie, Thieme-Verlag, Stuttgart.

In a preferred embodiment of the invention the polymerizable liquid crystalline mixtures comprise at least one inventive compound of formula I, at least one monofunctional compound of formulae VIa–VIm and at least one bifunctional polymerizable compound of formulae VIIa––VIIe.

In another preferred embodiment the polymerizable liquid crystalline mixtures comprise at least one inventive compound of formula I and at least two monofunctional compounds of formulae VIa–VIm.

Another feature of the invention is an anisotropic polymer film with an oriented chiral liquid crystalline phase obtainable by (co)polymerizing a liquid crystalline mixture comprising at least one compound of formula I and at least one polymerizable mesogenic compound preferably selected of formula VIa–VIm and VIIa–VIIe and/or at least one polymerizable compound of formula I.

The preparation of an anisotropic polymer film from a polymerizable mixture is generally described for example in D. J. Broer, et al., Angew. Makromol. Chem. 183, (1990), 45–66. The cholesteric polymerizable mixture is coated onto a substrate, aligned into uniform planar orientation, and polymerized in situ by exposure to heat or actinic radiation, thereby fixing the uniform alignment. Alignment and curing are carried out in the liquid crystal phase of the polymerizable mixture.

Actinic radiation means irradiation with light, like UV light, IR light or visible light, irradiation with X-rays or gamma rays or irradiation with high energy particles, such as ions or electrons. As a source for actinic radiation for example a single UV lamp or a set of UV lamps can be used. Another possible source for actinic radiation is a laser, like e.g. a UV laser, an IR laser or a visible laser.

For example, when photopolymerizing by means of UV light, a photoinitiator can be used that decomposes under UV irradiation to produce free radicals or ions that start the polymerization reaction. It is also possible to use a cationic photoinitiator, when curing polymerizable mesogens with for example vinyl and epoxide reactive groups, that photocures with cations instead of free radicals. As a photoinitiator for radical polymerization for example the commercially available Irgacure 651, Irgacure 184, Darocure 1173 or Darocure 4205 (all from Ciba Geigy AG) can be used, whereas in case of cationic photopolymerization the commercially available UVI 6974 (Union Carbide) can be used. Preferably the polymerizable liquid crystalline mixtures comprising polymerizable compounds of formula I and/or polymerizable mesogenic compounds of formulae VI and VII additionally comprise 0.01 to 10%, in particular 0.05 to 8%, very preferably 0.1 to 5% by weight of a photoinitiator, especially preferably a UV-photoinitiator.

Preferably polymerization is carried out under an atmosphere of inert gas, preferably under a nitrogen atmosphere.

As a substrate for example a glass or quarz sheet as well as a plastic film or sheet can be used. It is also possible to put a second substrate on top of the coated mixture prior to, during and/or after polymerization. The substrates can be removed after polymerization or not. When using two substrates in case of curing by actinic radiation, at least one substrate has to be transmissive for the actinic radiation used for the polymerization. Isotropic or birefringent substrates can be used. In case the substrate is not removed from the polymerized film after polymerization, preferably isotropic substrates are used.Preferably at least one substrate is a plastic substrate such as for example a film of polyester such as polyethyleneterephthalate (PET), of polyvinylalcohol (PVA), polycarbonate (PC) or triacetylcellulose (TAC), especially preferably a PET film or a TAC film. As a birefringent substrate for example an uniaxially stretched plastic film can be used. For example PET films are commercially available from ICI Corp. under the trade name Melinex.

The polymerizable mixture is preferably coated as a thin layer on a substrate or between substrate, and aligned in its liquid crystal phase, e.g. the nematic or smectic phase, to give a planar orientation, i.e. wherein the optical axis of the liquid crystal material is parallel to the plane of the layer. Planar orientation can be achieved for example by shearing the mixture, e.g. by means of a doctor blade. It is also possible to apply an alignment layer, for example a layer of rubbed polyimide or sputtered $SiO_x$, on top of at least one of the substrates. Alternatively, a second substrate is put on top of the coated material. In this case, the shearing caused by putting together the two substrates is sufficient to give good alignment. It is also possible to apply an electric or magnetic field to the coated mixture.

In some cases it is of advantage to apply a second substrate not only to aid alignment of the polymerizable mixture but also to exclude oxygen that may inhibit the polymerization. Alternatively curing can be carried out under an atmosphere of inert gas. However, curing in air is also possible using suitable photoinitiators and high lamp power. When using a cationic photoinitiator oxygen exclusion most often is not needed, but water should be excluded.

An inventive polymerizable liquid crystalline mixture for the preparation of anisotropic polymer films comprises preferably 0.1 to 35%, in particular 0.5 to 15% and very particularly preferably 0.5 to 5% by weight of one or more polymerizable chiral compounds of formula I Polymerizable liquid crystalline mixtures are preferred that comprise 1 to 3 chiral compounds of formula I.

The inventive polymerizable liquid crystalline mixtures can additionally comprise one or more other suitable components such as, for example, catalysts, sensitizers, stabilizers, inhibitors, co-reacting monomers, surface-active compounds, lubricating agents, wetting agents, dispersing agents, hydrophobing agents, adhesive agents, flow improvers, defoaming agents, deaerators, diluents, reactive diluents, auxiliaries, colourants, dyes or pigments.

Preferably the inventive polymerizable mixture comprises a stabilizer that is used to prevent undesired spontaneous polymerization for example during storage of the composition. As stabilizers in principal all compounds can be used that are known to the skilled in the art for this purpose. These compounds are commercially available in a broad variety. Typical examples for stabilizers are 4-ethoxyphenol or butylated hydroxytoluene (BHT).

It is also possible, in order to increase crosslinking of the polymers, to add a non mesogenic compound with two or more polymerizable functional groups, preferably in an amount of up to 20% by weight, to the polymerizable mixture alternatively or additionally to multifunctional mesogenic polymerizable compounds. Typical examples for difunctional non mesogenic monomers are alkyldiacrylates or alkyldimethacrylates with alkyl groups of 1 to 20 C atoms. Typical examples for non mesogenic monomers with more than two polymerizable groups are trimethylpropanetrimethacrylate or pentaerythritoltetraacrylate.

Polymerization of inventive compositions comprising compounds with only one polymerizable functional group leads to linear polymers, whereas in the presence of compounds with more than one polymerizable functional group crosslinked polymers are obtained.

For the preparation of anisotropic polymer gels, the liquid crystalline mixtures can be polymerized in situ as described above, however, in this case alignment of the polymerizable mixture is not always necessary.

Due to the presence of a photoisomerizable group in the compounds of formula I, the orientation of the inventive compounds and liquid crystalline mixtures can be changed by photoirradiation. Photoirradiation can be achieved for example with irradiation by UV light or other high energy sources such as lasers.

The compounds of formula I and the liquid crystalline mixtures and polymers comprising them are useful in optical and electrooptical devices like liquid crystal displays or projection systems, patterned films and optical elements like polarizers, retardation films, compensators, color filters, holographic elements or polarization beam splitters, as sensitizers, for photoswitching, in anisotropic membranes for the permeation of gases or fluids, adhesives, synthetic resins with anisotropic mechanical properties, cosmetic or pharmaceutical compositions, UV absorbers and sunscreens, diagnostics or liquid crystal pigments, for decorative and security applications, in nonlinear optics, optical information storage or as dopants.

The compounds of formula I and liquid crystalline mixtures, liquid crystal polymers or liquid crystal pigments comprising them are also suitable for use in cosmetic and pharmaceutical compositions, for example as UV absorbers or sunscreens for the protection of human skin or hair, in particular protection against UV-A and UV-B-radiation, as described for example in JP 04-134043.

A liquid crystalline mixture, liquid crystal polymer or liquid crystal pigment comprising a compound of formula I and reflecting UV light, in particular of a wavelength of 200 to 400 nm, is another feature of the invention. Another feature is a cosmetic composition, in particular a cosmetic or pharmaceutical composition for protection of human skin or hair, comprising as UV-filter a compound of formula I or a liquid crystalline mixture, liquid crystal polymer or liquid crystal pigment comprising a compound of formula I and reflecting UV light, in particular in a wavelength range of 200–440 nm, especially 280–400 nm, 200–230 nm (UV-C) and 280–330 nm (UV-B).

Furthermore, the compounds of formula I are particularly suitable for the preparation of patterned films, for example by the following method:

A thin layer of a polymerizable nematic mixture comprising an inventive photoisomerizable compound of formula I is coated as a thin film onto a substrate and aligned into planar orientation as described above. If the coated film is exposed to photoradiation of a suitable wavelength, the compound of formula I shows EZ isomerization if the wavelength of radiation is selected accordingly, e.g. between 300 and 400 nm. This causes a disruption of the planar nematic orientation in the exposed parts of the film, and can even lead to a radiation-induced nematic-isotropic phase transition in the exposed region. Thereby the birefringence is changing in the exposed parts. The partially or totally unoriented state can be fixed by subsequent in-situ polymerization, e.g. by thermal or photocuring.

If only a part of the film is exposed to photoradiation, e.g. by irradiation through a photomask that is applied on top of the coated film, the nematic orientation can be destroyed and the unoriented state subsequently be fixed by thermal or photocuring of the exposed parts. Afterwards the highly oriented state in the previously unexposed parts of the film is also fixed by thermal or photocuring. The sequence of these steps may also be changed, e.g. first fixing of the oriented parts by photocuring through a photomask, and then photoisomerization and fixing of the remaining parts.

The above described methods can also be used to prepare patterned films with chiral liquid crystalline structure, such as e.g. cholesteric or chiral smectic C liquid crystal films.

For example cholesteric liquid crystal films with planar alignment show selective reflection of visible light that is circularly polarized, caused by interaction of incident light with the helically twisted structure of the cholesteric material. If one or more chiral compounds of formula I are added e.g. to nematic or cholesteric polymerizable liquid crystal mixture, photoisomerization of the chiral compounds of formula I leads to a change of their chirality and thus to a change of the helical pitch of the mixture, which is fixed by polymerization. As the pitch is directly proportional to the reflection wavelength of the cholesteric material, patterned cholesteric films having regions of different reflection wavelength can be obtained by using photomask technique as described above.

Such films are suitable for example as color filters in optical or electrooptical devices like liquid crystal displays or projectors. They can also be used for security markings, e.g. to identify or prevent falsification of credit cards, passports, bank notes or other documents of value, for decorative coatings or the preparation of liquid crystal pigments.

Furthermore, cholesteric reflective films exhibiting a change of the pitch in vertical direction, i.e. perpendicular to the film plane, can be prepared. They can be used as broadband reflective polarizers having a broad bandwidth of the reflected wavelength band.

The preparation of patterned cholesteric films is described for example in WO 00/34808 and in P. van de Witte et al., J. Mater. Chem. 9 (1999), 2087–2094, the entire disclosure of which is incorporated into this application by way of reference.

A broadband reflective cholesteric film can e.g. be prepared as follows: A layer of a cholesteric or nematic mixture with planar orientation comprising a chiral photoisomerizable compound of formula I additionally comprises a dye having an absorption maximum at the wavelength where the isomerizable compound shows photoisomerization. For example, the mixture may comprise an isomerizable compound showing isomerization at a wavelength in the UV range together with a UV dye. If the mixture is exposed to UV radiation as described above, the dye will create a gradient in UV light intensity throughout the thickness of the layer. As a consequence, the isomerization is faster at the top of the layer than at the bottom and a pitch gradient is created, leading to a broadening of the reflected wavelength band. The pitch gradient and reflection bandwidth can be controlled for example by varying the film thickness, irradiation time, radiation dose and/or the concentration of the UV dye and the photoisomerizable compound. If the cholesteric mixture comprises one or more polymerizable components, the structure of the film can be fixed by in-situ polymerization.

It is also possible to prepare cholesteric liquid crystal films wherein the pitch varies in horizontal or vertical direction by using an achiral isomerizable compound of formula I together with a cholesteric liquid crystal mixture. As described above, the achiral isomerizable compound changes its shape e.g. due to EZ isomerization under photoirradiation, causing a change of the order parameter and thus of the pitch in the cholesteric mixture in the irradiated regions. If the mixture contains a polymerizable compound, the region with different pitch can be fixed by subsequent in-situ polymerization. Thereby, patterned cholesteric films having regions of different reflection wavelength can be obtained by using photomask technique as described above. Alternatively, a broadband cholesteric film with the pitch varying in vertical direction can be obtained by using e.g. a UV dye that creates an intensity gradient of the photoradiation in vertical direction as described above.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius; and, unless otherwise indicated, all parts and percentages are by weight.

The entire disclosure of all applications, patents and publications, cited above, and corresponding European Application No. 01108720.2, filed Apr. 6, 2001, is hereby incorporated by reference. The following abbreviations are used to illustrate the liquid crystalline phase behaviour of the compounds: K=crystalline; N=nematic; S=smectic; N*, Ch=chiral nematic or cholesteric; I=isotropic. The numbers between these symbols indicate the phase transition temperatures in degree Celsius. Furthermore, mp. is the melting point, $\Delta n$ is the birefringence at 589 nm and 20° C. and $\Delta \in$ is the dielectric anisotropy at 20° C. C* in a chemical formula denotes a chiral C atom. DCM is dichloromethane.

"Conventional workup" means: water is added if necessary, the mixure is extracted with methylene chloride, diethyl ether or toluene, the phases are separated, the organic phase is dried and concentrated by evaporation, and the product is purified by crystallization and/or chromatography.

EXAMPLES

Example 1

Compound (1) was prepared according to the following reaction scheme

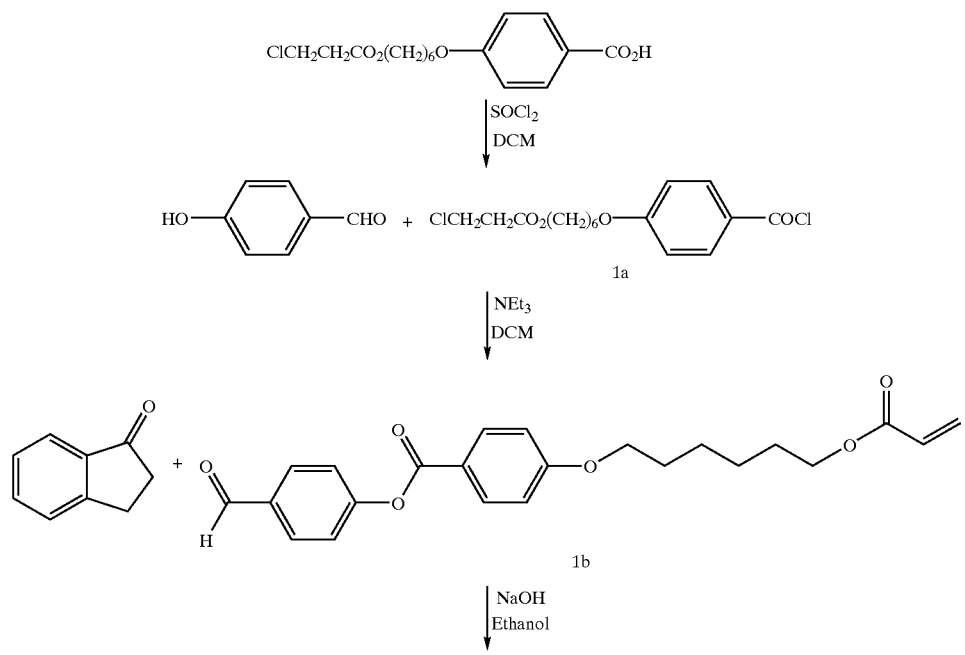

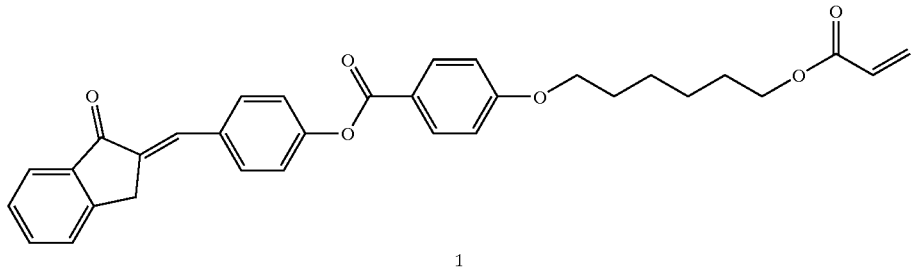

1

3-Chloro-propionic acid 6-(4-chlorocarbonyl-phenoxy)-hexyl ester (1a)

HHBA-3-chloropropionate (15.0 g, 45.6 mmol) was stirred with thionyl chloride (4.4 ml, 60.3 mmol, 1.3 equiv.) and a catalytic amount of N-methyl pyrrolidone under reflux in DCM for 16 hours. The mixture was cooled and evaporated to dryness to leave an oily residue. Yield=16.2 g, 100%. The product was used without further purification in the next step.

4-(6-Acryloyloxy-hexyloxy)-benzoic acid 4-formyl-phenyl ester (1b)

Acid chloride (15.5 g, 45.6 mmol), 4-hydroxybenzaldehyde (5.6 g, 45.6 mmol) and triethylamine (25.4 ml, 183 mmol) were stirred in DCM at 35° C. overnight. The mixture was cooled to room temperature, the DCM layer was washed with water, then dilute hydrochloric acid then dried ($Na_2SO_4$). Evaporation of the solvent left a pale pink solid residue. This was used without further purification.

Compound (1)

1-Indanone (2.31 g, 0.017 mol) was dissolved in ethanol (12 ml), and was added to sodium hydroxide (0.23 g, 0.005 mol) dissolved in water (4 ml) and ethanol (1.5 ml) and was left to stir for 20 min. 2 (6.76 g, 0.017 mol) in ethanol (20 ml) was added to the mixture and it was left to stir. After 16 h, a solid precipitate was removed by vacuum filtration and was washed with cold ethanol (2×20 ml). Yield 0.72 g, 8% $^1$H NMR and $^{13}$C NMR gave expected signals. Mass spec. ES+, 533.1 (M+Na$^+$), 1732.15 (2M+Na$^+$).

Transition Temperatures:

K-124-131-I (first heat)
I-130-N-109-K (first cool)
K-131-I (second heat)
I-123-N-110-K (second cool)

Example 2

Compound (2) was prepared according to the following reaction scheme

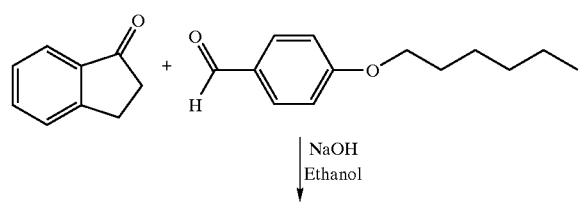

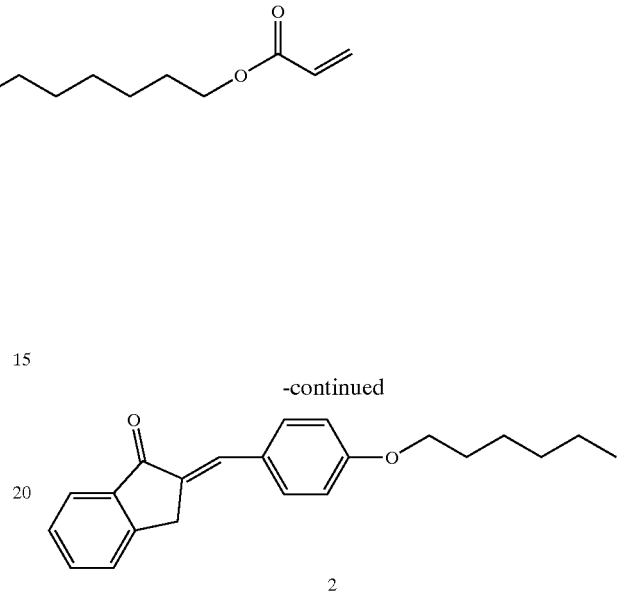

2

2-(4-Hexyloxy-benzylidene)-indan-1-one (2)

1-Indanone (4.17 g, 0.032 mol) was dissolved in ethanol (20 ml), and was added to sodium hydroxide (0.44 g, 0.011 mol) dissolved in water (8 ml) and ethanol (3 ml) and was left to stir for 20 min. 4-(Hexyloxy)benzaldehyde (6.4 ml, 0.031 mol), dissolved in ethanol (35 ml), was added to the mixture and was stirred for 4 hours. The product was isolated by vacuum filtration and was washed with cold ethanol (2×20 ml) and was dried in a vacuum oven. Yield= 8.47 g, 85%. $^1$H NMR and $^{13}$C NMR gave expected signals.

Melting point 101° C., (K–I, ΔH=8399 cal mol$^{-1}$).

Example 3

Photoisomerisation of (1) in a polymerizable liquid crystal mixture

The following polymerizable mixture was prepared:

| | |
|---|---|
| Compound (1) | 10% |
| Compound (A) | 20% |
| Compound (B) | 70% |

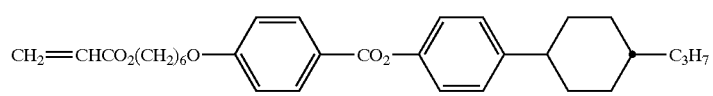
(A)

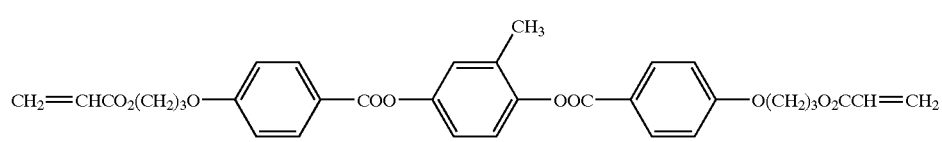
(B)

Compound (A) is described in WO 98/00428. Compound (B) can be prepared as described in D. J. Broer et al., Makromol. Chem. 190, 3201–3215 (1989).

The above mixture was dissolved in THF (20% w/w of mixture in THF). A film of the above mixture was made by spin coating the solution onto rubbed PI coated glass at 3000 rpm. The film was slightly opaque when viewed in transmission. The film was then annealed at 100° C. for 30 seconds, whereupon the alignment of the film improved, and the film became transparent. When viewed between crossed polariser, the film had maximum transmission when the rubbing direction was at 45° to the stretch direction of the polariser, and minimum transmission when the rubbing direction was parallel or perpendicular to the polariser stretch direction. The film was then exposed to 360 nm UV light through a plastic mask (black ink on a PET substrate) from a high-pressure mercury lamp at 18 mW/cm² for 10 minutes. When the exposed film was viewed between crossed polarisers, with the rubbing direction at 45° to the stretch direction of the polarisers, then the areas which had experience a higher exposure to the UV light showed lower transmission compared to the unexposed areas.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A compound of formula I

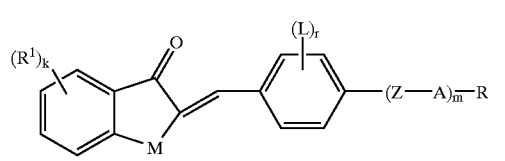
(I)

wherein
M is $(CH_2)_i$, wherein one $CH_2$ group may also be replaced by $NR^0$, O or S, where M is not S, $SCH_2$, or $OCH_2$,
i is 1, 2, 3 or 4,
$R^0$ is H or alkyl with 1–4 C atoms,
L is halogen, CN, SCN, $NO_2$, $SF_5$ or an alkyl, alkoxy, alkylcarbonyl or alkoxycarbonyl group with 1–4 C atoms, wherein one or more H atoms may be substituted with F or Cl,
r is 0, 1, 2, 3 or 4,
$R^1$ is in each case independently OH, O—B, $OCH_2$B or has one of the meanings of R given below,
k is 0, 1, 2, 3 or 4,
A and B are independently of each other an aromatic or alicyclic group with 4–12 C-atoms,
Z is in each case independently —O—, —S—, —CO—, —COO—, —OCO—, —CO—$NR^0$—, —$NR^0$—CO—, —$CH_2CH_2$—, —$CF_2CF_2$—, —$CH_2CF_2$—, —$OCH_2$—, —$CH_2O$—, —$SCH_2$—, —$CH_2S$—, —$CF_2O$—, —$OCF_2$—, —CH=CH—, —CF=CF—, —CH=CF—, —$(CH_2)_4$—, —CH=CH—COO—, —OCO—CH=CH—, —OOC—$CHR^{00}$—OOC—, —COO—$CHR^{00}$—COO—, —C≡C— or a single bond,
$R^{00}$ is straight chain or branched alkyl or alkoxy with 1–8 C atoms or phenyl that is optionally mono- or polysubstituted by L,
m is 0, 1 or 2,
R is halogen, $NO_2$, CN, SCN, $SF_5$, straight chain, branched or cyclic alkyl with 1–25 C atoms wherein one or more $CH_2$ groups can also be replaced by —O—, —S—, —CO—, —$NR^0$—, —CH=CH—, —C≡—C— in such a manner that O and/or S atoms are not linked directly to one another, and wherein one or more H-atoms can also be replaced by F or Cl or phenyl that is optionally mono- or polysubstituted by L, or is P-(Sp-X)$_n$—,
P is a polymerizable group,
Sp is a spacer group with 1–20 C atoms,
X has one of the meanings of Z, and
n is 0 or 1.

2. An optical or an electrooptical device, a patterned film, an optical element a sensitizer, an anisotropic membrane for the permeation of gases or fluids, an adhesive, a synthetic resin with anisotropic mechanical properties, a cosmetic or pharmaceutical composition, an UV absorber, a sunscreen, a diagnostic or a liquid crystal pigment, an optical information storage or a dopant comprising a photoisomerizable compound according to claim 1.

3. A compound according to claim 1, wherein m is 1 or 2.

4. A compound according to claim 1, wherein at least one of R and $R^1$ is P-(Sp-X)$_n$—.

5. A compound according to claim 1, wherein
A is in each case independently 1,4-phenylene wherein, optionally, one or more CH groups are replaced by N, 1,4-cyclohexylene wherein, optionally, one or two non-adjacent $CH_2$ groups are replaced by O and/or S, 1,3-dioxolane-4,5-diyl, 1,4-cyclohexenylene, piperidine-1,4-diyl, pyrrolidine-2,4-diyl, 1,4-bicyclo-(2,2,2)-octylene, naphthalene-2,6-diyl, decahydronaphthalene-2,6-diyl, 1,2,3,4-tetrahydronaphthalene-2,6-diyl or indane-2,5-diyl, all these groups are unsubstituted, or optionally mono- or polysubstituted with L.

6. A compound according to claim 1, wherein the group
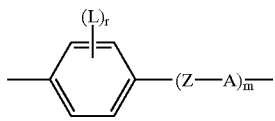
in formula I is selected from the formulae
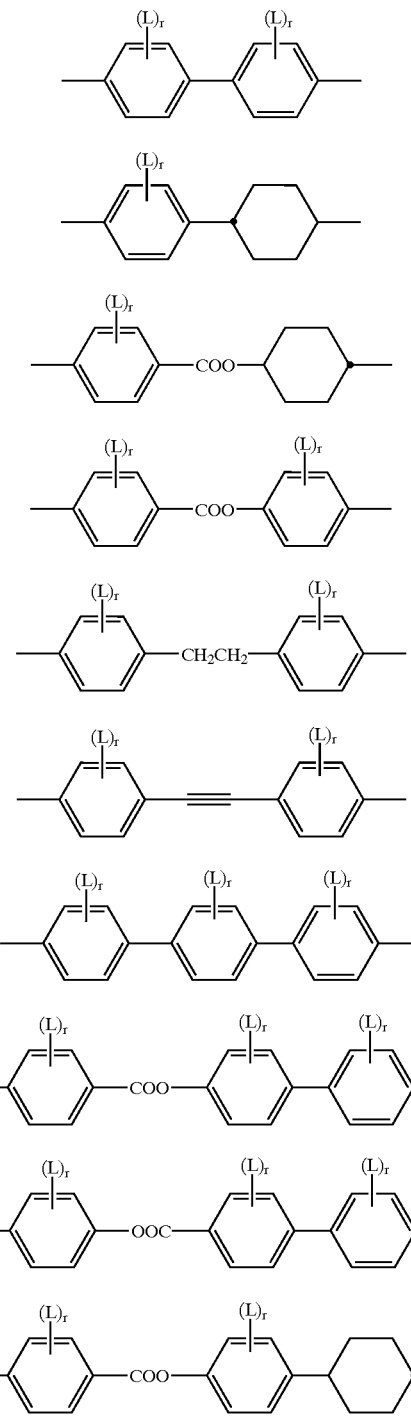
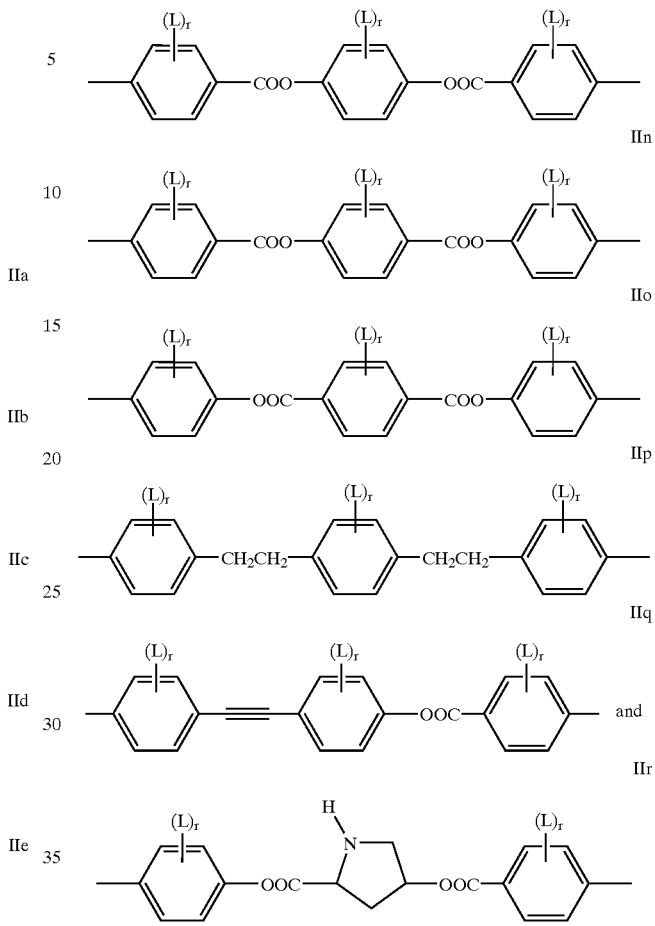
wherein r is 0, 1 or 2.
7. A compound according to claim 1, of the subformulae
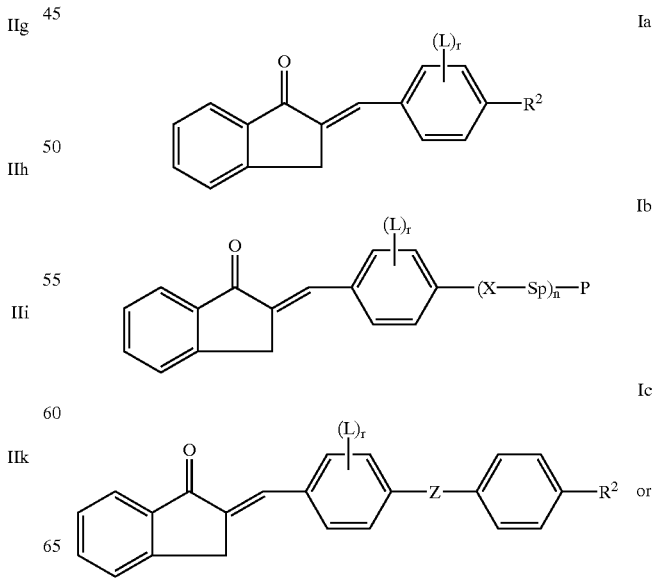

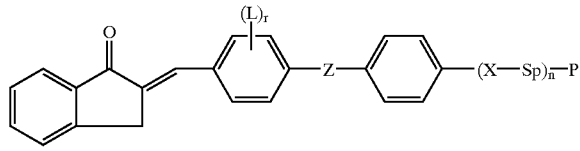

wherein
- Z is in each case independently —O—, —S—, —CO—, —COO—, —OCO—, —CO—NR⁰—, —NR⁰—CO—, —CH₂CH₂—, —CF₂CF₂—, —CH₂CF₂—, —OCH₂—, —CH₂O—, —SCH₂—, —CH₂S—, —CF₂O—, —OCF₂—, —CH=CH—, —CF=CF—, —CH=CF—, —(CH₂)₄—, —CH=CH—COO—, —OCO—CH=CH—, —OOC—CHR⁰⁰—OOC—, —COO—CHR⁰⁰—COO—, —C≡—C— or a single bond,
- P is a polymerizable group,
- Sp is a spacer group with 1–20 C atoms,
- X has one of the meanings of Z, and
- L is halogen, CN, SCN, NO₂, SF₅ or an alkyl, alkoxy, alkylcarbonyl or alkoxycarbonyl group with 1–4 C atoms, wherein one or more H atoms may be substituted with F or Cl,
- n is 0 or 1,
- r is 0, 1, 2, 3 or 4,
- R⁰⁰ is straight chain or branched alkyl or alkoxy with 1–8 C atoms or phenyl that is optionally mono- or polysubstituted by L,
- R² is H, halogen, NO₂, CN, SCN, SF₅, straight chain, branched or cyclic alkyl with 1–25 C atoms wherein one or more CH₂ groups can also be replaced by —O—, —S—, —CO—, —NR⁰—, —CH=CH—, —C≡C— in such a manner that O and/or S atoms are not linked directly to one another, and wherein one or more H-atoms can also be replaced by F or Cl, wherein R⁰ is H or alkyl with 1–4 C atoms.

8. A compound according to claim 1, wherein P is selected from
CH₂=CW¹—COO—,

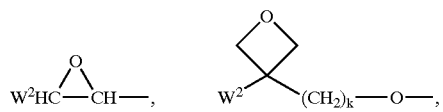

CH₂=CW²—O—, CH₃—CH=CH—O—, HO—CW²W³—, HS—CW²W³—, HW²N—, HO—CW²W³—NH—, CH₂=CW¹—CO—NH—, CH₂=CH—(COO)_{k1}-Phe-(O)_{k2}—, Phe-CH=CH—, HOOC—, OCN— and W⁴W⁵W⁶Si—, with W¹ being H, Cl, CN, phenyl or alkyl with 1–5 C-atoms, W² and W³ being independently of each other H or alkyl with 1 to 5 C-atoms, W⁴, W⁵ and W⁶ being independently of each other Cl, oxaalkyl or oxacarbonylalkyl with 1 to 5 C-atoms, Phe being 1,4-phenylene and k₁ and k₂ being independently of each other 0 or 1.

9. A compound according to claim 1, wherein R and/or R¹ is an alkyl or alkoxy group with 1–12 C atoms.

10. A liquid crystalline mixture comprising at least one compound according to claim 1.

11. A liquid crystalline mixture according to claim 10 further comprising at least one polymerizable compound of formula I or another polymerizable compound.

12. A linear or crosslinked anisotropic polymer made by polymerizing a mixture according to claim 11.

13. An optical or an electrooptical device, a patterned film, an optical element, a polarizer, a retardation film, a compensator, a color filter, a holographic element, a polarization beam splitter, a photoswitching device, a decorative or security system, a non-linear optical device, a sensitizer, an anisotropic membrane for the permeation of gases or fluids, an adhesive, a synthetic resin with anisotropic mechanical properties, a cosmetic or a pharmaceutical composition, an UV absorber, a sunscreen, a diagnostic or a liquid crystal pigment, or an optical information storage device comprising a linear or crosslinked anisotropic polymer according to claim 12.

14. A polymer film made by coating a polymerizable mixture according to claim 11 onto a substrate, aligning the mixture into uniform orientation, and polymerizing the mixture, wherein at least a part of the mixture before or during polymerization is exposed to actinic radiation of a wavelength where the compound of formula I shows photoisomerization.

15. A polymer film according to claim 14 showing a pattern of at least two regions having different orientation.

16. A polymer film according to claim 14, showing a pattern of at least two regions having different birefringence.

17. A polymer film according to claim 16, wherein the polymer film is a nematic film.

18. A polymer film according to claim 14, showing a pattern of at least one region with an oriented state and at least one region with a partially or totally unoriented state.

19. A polymer film according to claim 18, wherein the polymer film is a nematic film.

20. A polymer film according to claim 14, wherein the polymer film is a patterned cholesteric film having planar alignment and regions of different reflection wavelength.

21. A polymer film according to claim 14, wherein the polymer film is a broadband reflective cholesteric film.

22. A polymer film according to claim 14, wherein the polymer film is a cholesteric film having a pitch vary in a horizontal or vertical direction, prepared from an achiral isomerizable compound of formula I together with a cholesteric liquid crystal mixture.

23. A mixture according to claim 11, comprising at least one compound of formulae VIa to VIIe:

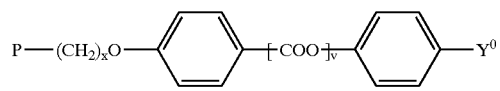
(VIa)

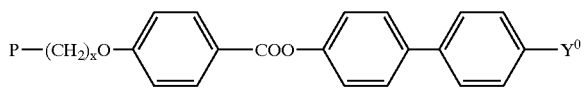
(VIb)

-continued
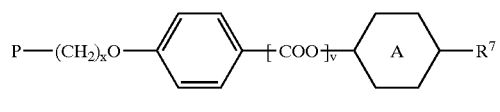
(VIc)
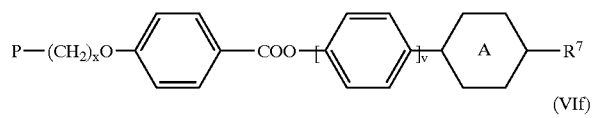
(VId)
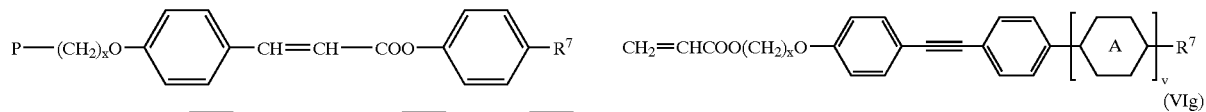
(VIe)
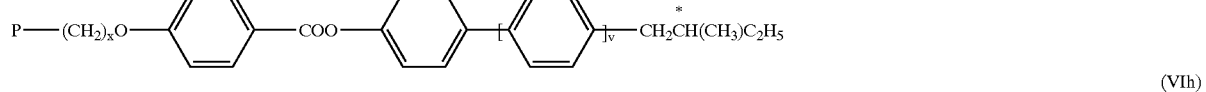
(VIf)
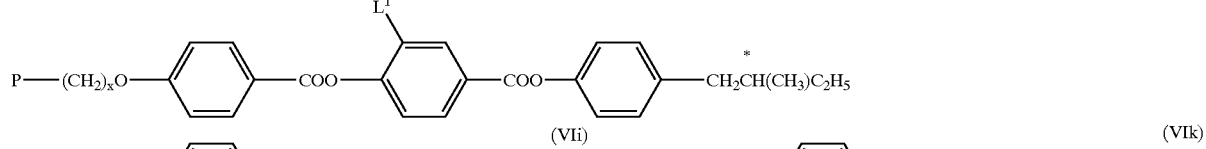
(VIg)
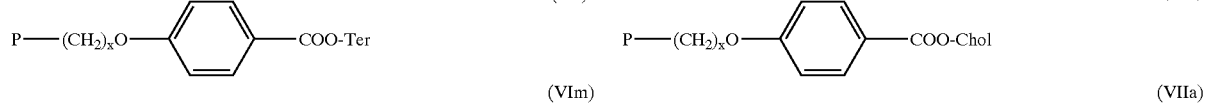
(VIh)
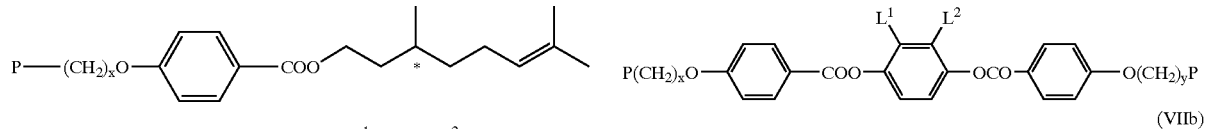
(VIi)
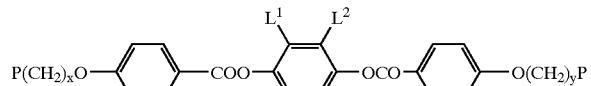
(VIk)
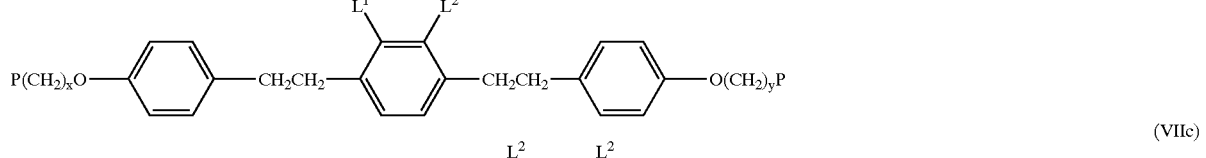
(VIm)
(VIIa)
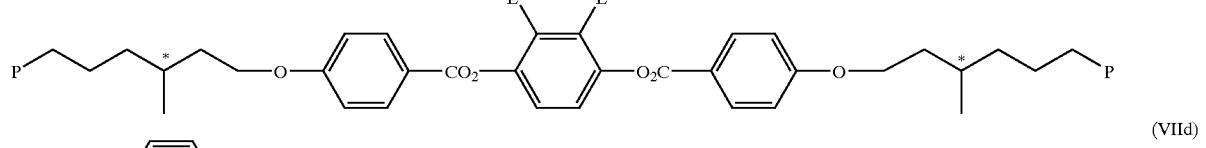
(VIIb)
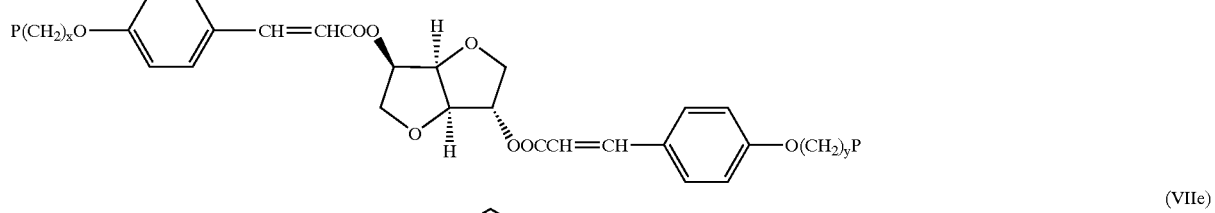
(VIIc)
(VIId)
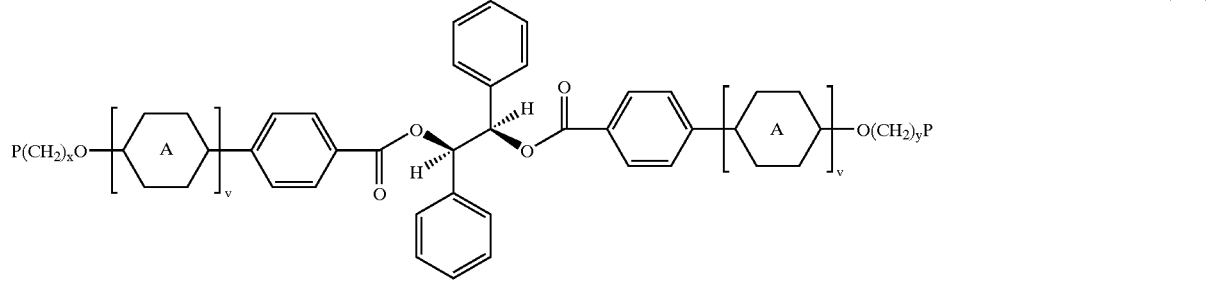
(VIIe)
Wherein
  P is a polymerizable group,
  x and y are identical or different integers from 1 to 12,
  A is 1,4-phenylene or 1,4-cyclohexylene,
  v is 0 or 1,
  $Y^0$ is a polar group,
  $R^7$ is an unpolar alkyl or alkoxy group,
  Ter is a terpenoid radical,
  Chol is a cholesteryl group, and $L^1$ and $L^2$ are each independently H, F, Cl, CN, OH, $NO_2$ or an optionally halogenated alkyl, alkoxy or carbonyl group with 1 to 7 C atoms.

24. A compound according to claim 23, wherein $Y^0$ is CN, $NO_2$, halogen, $OCH_3$, OCN, SCN, $COR^8$, $COOR^8$ or a mono- oligo- or polyfluorinated alkyl or alkoxy group with 1 to 4 C atoms, $R^8$ is optionally fluorinated alkyl with 1 to 4, C atoms, and $R^7$ is an alkyl group with 1 to 15 C atoms or an alkoxy group with 2 or to 15 C atoms.

25. An optical or an electrooptical device, a patterned film, an optical element, a polarizer, a retardation film, a compensator, a color filter, a holographic element, a polarization beam splitter, a photoswitching device, a decorative or security system, a non-linear optical device, a sensitizer, an anisotropic membrane for the permeation of gases or fluids, an adhesive, a synthetic resin with anisotropic mechanical properties, a cosmetic or a pharmaceutical composition, an UV absorber, a sunscreen, a diagnostic or a liquid crystal pigment, or an optical information storage device comprising a liquid crystalline mixture according to claim 10.

26. A liquid crystal display comprising a compound according to claim 1.

27. A polarizer, a retardation film, a compensator, a color filter, a holographic element, or a polarization beam splitter, a photoswitching device, a decorative or security system, or a non-linear optical device comprising a photoisomerizable compound according to claim 1.

28. A compound according to claim 1, wherein M is $NR^0$, O, $(CH_2)_2$, or $NR^0$—$CH_2$, wherein $R^0$ H or alkyl with 1–4 atoms.

29. A compound according to claim 1, wherein M is $CH_2$ or $(CH_2)_2$.

30. A compound of formula I

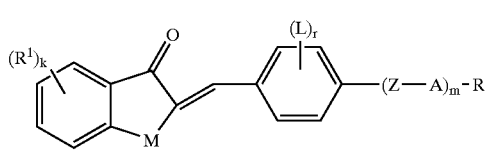

(I)

wherein

M is $(CH_2)_i$, wherein one $CH_2$ group may also be replaced by $NR^0$, O or S, i is 1, 2, 3 or 4, L is halogen, CN, SCN, $NO_2$, $SF_5$ or an alkyl, alkoxy, alkylcarbonyl or alkoxycarbonyl group with 1–4 C atoms, wherein one or more H atoms may be substituted with F or Cl, r is 0, 1, 2, 3 or 4, $R^1$ is in each case independently OH, O—B, $OCH_2B$ or has one of the meanings of R given below, k is 0, 1, 2, 3 or 4, A and B are independently of each other an aromatic or alicyclic group with 4–12 C-atoms, Z is in each case independently —O—, —S—, —CO—, —COO—, —OCO—, —CO—$NR^0$—, —$NR^0$—CO—, —$CH_2CH_2$—, —$CF_2CF_2$—, —$CH_2CF_2$—, —$OCH_2$—, —$CH_2O$—, —$SCH_2$—, —$CH_2S$—, —$CF_2O$—, —$OCF_2$—, —CH=CH—, —CF=CF—, —CH=CF—, —$(CH_2)_4$—, —CH=CH—COO—, —OCO—CH=CH—, —OOC—$CHR^{00}$—OOC—, —COO—$CHR^{00}$—COO—, —C≡C— or a single bond, $R^{00}$ is straight chain or branched alkyl or alkoxy with 1–8 C atoms or phenyl that is optionally mono- or polysubstituted by L, m is 1 or 2, R is H, halogen, $NO_2$, CN, SCN, $SF_5$, straight chain, branched or cyclic alkyl with 1–25 C atoms wherein one or more $CH_2$ groups can also be replaced by —O—, —S—, —CO—, —$NR^0$—, —CH=CH—, —C≡C— in such a manner that O and/or S atoms are not linked directly to one another, and wherein one or more H-atoms can also be replaced by F or Cl or phenyl that is optionally mono- or polysubstituted by L, or is P-(Sp-X)$_n$—, $R^0$ is H or alkyl with 1–4 C atoms, P is a polymerizable group, Sp is a spacer group with 1–20 C atoms, X has one of the meanings of Z, and n is 0 or 1.

31. A compound according to claim 30, wherein M is $NR^0$, O, S, $CH_2$, $(CH_2)_2$, $NR^0$—$CH_2$, O—$CH_2$ or S—$CH_2$, and $R^0$ is H or alkyl with 1–4 C atoms.

32. An optical or an electrooptical device, a patterned film, an optical element, a sensitizer, an anisotropic membrane for the permeation of gases or fluids, an adhesive, a synthetic resin with anisotropic mechanical properties, a cosmetic or a pharmaceutical composition, an UV absorber, a sunscreen, a diagnostic or a liquid crystal pigment, an optical information storage device or a dopant comprising a photoisomerizable compound according to claim 30.

33. A compound according to claim 30, wherein

R is halogen, $NO_2$, CN, SCN, $SF_5$, straight chain, branched or cyclic alkyl with 1–25 C atoms wherein one or more $CH_2$ groups can also be replaced by —O—, —S—, —CO—, —$NR^0$—, —CH=CH—, —C≡C— in such a manner that O and/or S atoms are not linked directly to one another, and wherein one or more H-atoms can also be replaced by F or Cl or phenyl that is optionally mono- or polysubstituted by L, or is P-(Sp-X)$_n$—.

34. A polymer film showing a pattern of at least two regions having different orientation made by a coating a liquid crystalline polymerizable mixture comprising at least one or more polymerizable compounds onto a substrate, aligning the mixture into uniform orientation, and polymerizing the mixture, wherein at least a part of the mixture before or during polymerization is exposed to actinic radiation of a wavelength wherein at least one compound shows photoisomerization.

35. A polymer film according to claim 34, showing a pattern of at least two regions having different birefringence.

36. A polymer film according to claim 35, wherein the polymer film is a nematic film.

37. A polymer film according to claim 34, showing a pattern of at least one region with an oriented state and at least one region with a partially or totally unoriented state.

38. A polymer film according to claim 37, the polymer film is a nematic film.

39. A compound of formula I

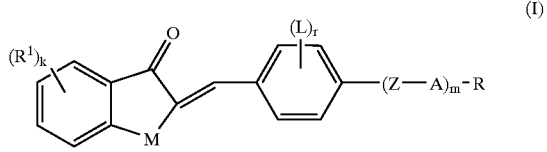

(I)

wherein

M is $(CH_2)_i$, wherein one $CH_2$ group may also be replaced by $NR^0$, O or S, $R^0$ is H or alkyl with 1–4 C atoms, i is 1, 2, 3 or 4, L is halogen, CN, SCN, $NO_2$, $SF_5$ or an alkyl, alkoxy, alkylcarbonyl or alkoxycarbonyl group with 1–4 C atoms, wherein one or more H atoms may be substituted with F or Cl, r is 0, 1 or 2, $R^1$ is in each case independently OH, O—B, $OCH_2$B or has one of the meanings of R given below, k is 0, 1, 2, 3 or 4, B independent of A, is an aromatic or alicyclic group with 4–2 C-atoms, $R^{00}$ is straight chain or branched alkyl or alkoxy with 1–8 C atoms or phenyl that is optionally mono- or polysubstituted by L, R is H, halogen, $NO_2$, CN, SCN, $SF_5$, straight chain, branched or cyclic alkyl with 1–25 C atoms wherein one or more $CH_2$ groups can also be replaced by —O—, —S—, —CO—, —$NR^0$—, —CH=CH—, —C≡C— in such a manner that O and/or S atoms are not linked directly to one another, and wherein one or more H-atoms can also be replaced by F or Cl or phenyl that is optionally mono- or polysubstituted by L, or is P-(Sp-X)$_n$—, $R^0$ is H or alkyl with 1–4 C atoms, P is a polymerizable group, Sp is a spacer group with 1–20 C atoms, X has one of the meanings of Z, and n is 0 or 1, wherein the group

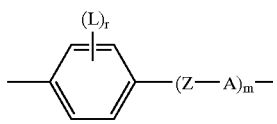

in formula I is selected from the formulae

IIa
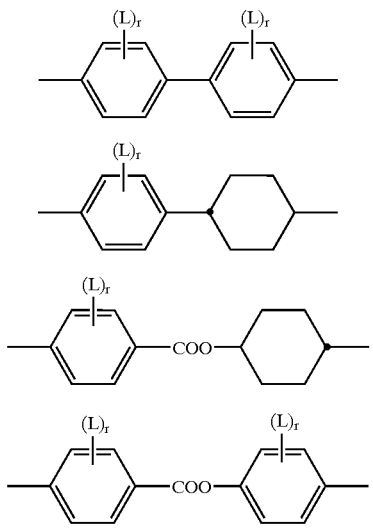

IIb

IIc

IId

IIe
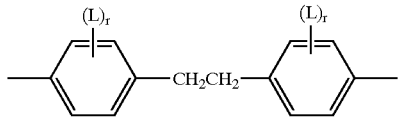

IIf

IIg
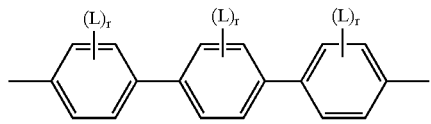

IIh
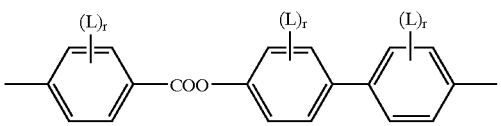

IIi
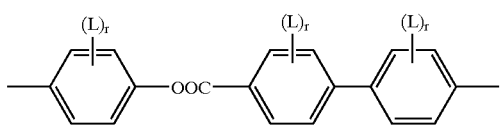

IIk
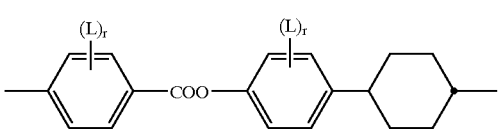

IIm
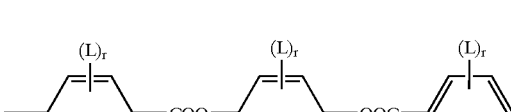

IIn
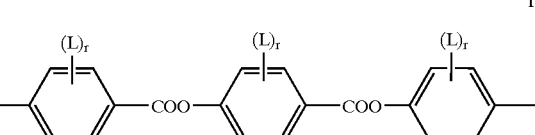

IIo
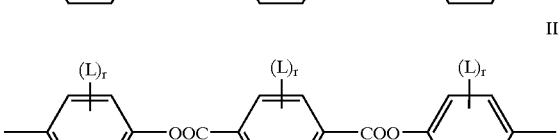

IIp
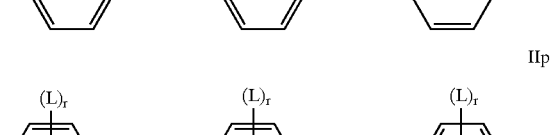

IIq
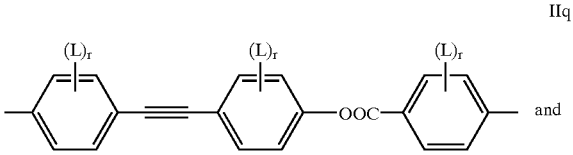 and

-continued

IIr

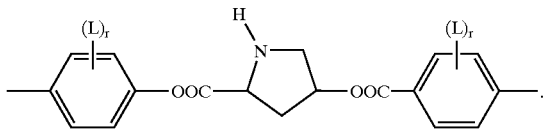

40. A compound of the formulae

Ia

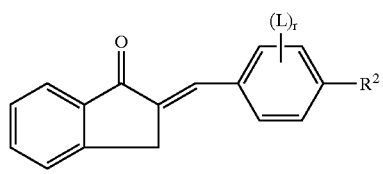

Ib

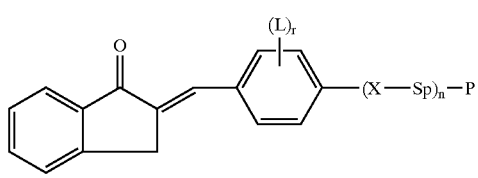

Ic

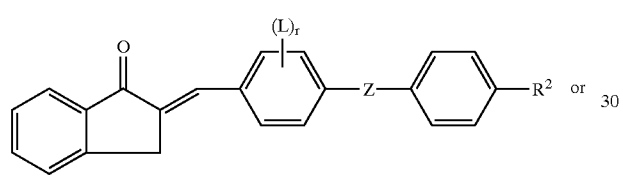

Id

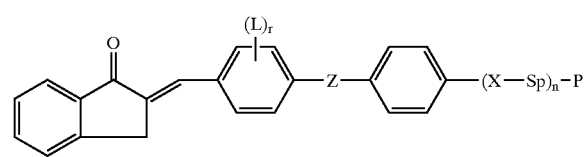

wherein

Z is in each case independently —O—, —S—, —CO—, —COO—, —OCO—, —CO—NR$^0$—, —NR$^0$—CO—, —CH$_2$CH$_2$—, —CF$_2$CF$_2$—, —CH$_2$CF$_2$—, —OCH$_2$—, —CH$_2$O—, —SCH$_2$—, —CH$_2$S—, —CF$_2$O—, —OCF$_2$—, —CH=CH—, —CF=CF—, —CH=CF—, —(CH$_2$)$_4$—, —CH=CH—COO—, —OCO—CH=CH—, —OOC—CHR$^{00}$—OOC—, —COO—CHR$^{00}$—COO—, —C≡C— or a single bond, P is a polymerizable group, Sp is a spacer group with 1–20 C atoms, X has one of the meanings of Z, L is halogen, CN, SCN, NO$_2$, SF$_5$ or an alkyl, alkoxy, alkylcarbonyl or alkoxycarbonyl group with 1–4 C atoms, wherein one or more H atoms may be substituted with F or Cl, n is 0 or 1, r is 0, 1, 2, 3 or 4, R$^{00}$ is straight chain or branched alkyl or alkoxy with 1–8 C atoms or phenyl that is optionally mono- or polysubstituted by L, R$^2$ is H, halogen, NO$_2$, CN, SCN, SF$_5$, straight chain, branched or cyclic alkyl with 1–25 C atoms wherein one or more CH$_2$ groups can also be replaced by —O—, —S—, —CO—, —NR$^0$—, —CH=CH—, —C≡C— in such a manner that O and/or S atoms are not linked directly to one another, and wherein one or more H-atoms can also be replaced by F or Cl, and R$^0$ is H or alkyl with 1–4 C atoms.

41. A polymer film showing a pattern of at least two regions having different orientation made by:

coating a liquid crystalline polymerizable mixture comprising at least one compound of formula I

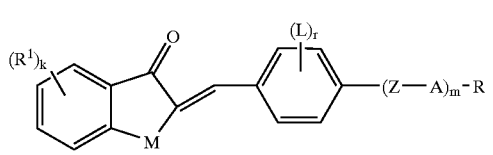 (I)

wherein

M is (CH$_2$)$_i$, wherein one CH$_2$ group may also be replaced by NR$^0$, O or S, i is 1, 2, 3 or 4, L is halogen, CN, SCN, NO$_2$, SF$_5$ or an alkyl, alkoxy, alkylcarbonyl or alkoxycarbonyl group with 1–4 C atoms, wherein one or more H atoms may be substituted with F or Cl, r is 0, 1, 2, 3 or 4, R$^1$ is in each case independently OH, O—B, OCH$_2$B or has one of the meanings of R given below, k is 0, 1, 2, 3 or 4, A and B are independently of each other an aromatic or alicyclic group with 4–12 C-atoms, Z is in each case independently —O—, —S—, —CO—, —COO—, —OCO—, —CO—NR$^0$—, —NR$^0$—CO—, —CH$_2$CH$_2$—, —CF$_2$CF$_2$—, —CH$_2$CF$_2$—, —OCH$_2$—, —CH$_2$O—, —SCH$_2$—, —CH$_2$S—, —CF$_2$O—, —OCF$_2$—, —CH=CH—, —CF=CF—, —CH=CF—, —(CH$_2$)$_4$—, —CH=CH—COO—, —OCO—CH=CH—, —OOC—CHR$^{00}$—OOC—, —COO—CHR$^{00}$—COO—, —C≡C— or a single bond, R$^{00}$ is straight chain or branched alkyl or alkoxy with 1–8 C atoms or phenyl that is optionally mono- or polysubstituted by L, m is 0, 1 or 2, R is H, halogen, NO$_2$, CN, SCN, SF$_5$, straight chain branched or cyclic alkyl with 1–25 C atoms wherein one or more CH$_2$ groups can also be replaced by —O—, —S—, —CO—, —NR$^0$—, —CH=CH—, —C≡C— in such a manner that O and/or S atoms are not linked directly to one another, and wherein one or more H-atoms can also be replaced by F or Cl or phenyl that is optionally mono- or polysubstituted by L, or is P-(Sp-X)$_n$—, R$^0$ is H or alkyl with 1–4 C atoms, P is a polymerizable group, Sp is a spacer group with 1–20 C atoms, X has one of the meanings of Z, and n is 0 or 1, and at least one polymerizable compound of formula I or another polymerizable compound, onto a substrate, aligning the mixture into uniform orientation, and polymerizing the mixture, wherein at least a part of the mixture before or during polymerization is exposed to actinic radiation of a wavelength where the compound of formula I shows photoisomerization.

42. A compound of formula I

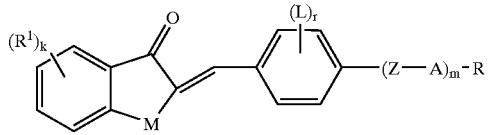

wherein
M is (CH$_2$)$_i$, wherein one CH$_2$ group may also be replaced by NR$^0$, O or S, where M is not S,
i is 1, 2, 3 or 4,
R$^0$ is H or alkyl with 1–4 C atoms,
L is halogen, CN, SCN, NO$_2$, SF$_5$ or an alkyl, alkoxy, alkylcarbonyl or alkoxycarbonyl group with 1–4 C atoms, wherein one or more H atoms may be substituted with F or Cl,
r is 0, 1, 2, 3 or 4,
R$^1$ is in each case independently OH, O—B, OCH$_2$B or has one of the meanings of R given below, and wherein at least one R$^1$ is other than H,
k is 1, 2, 3 or 4,
A and B are independently of each other an aromatic or alicyclic group with 4–12 C-atoms,
Z is in each case independently —O—, —S—, —CO—, —COO—, —OCO—, —CO—NR$^0$—, —NR$^0$—CO—, —CH$_2$CH$_2$—, —CF$_2$CF$_2$—, —CH$_2$CF$_2$—, —OCH$_2$—, —CH$_2$O—, —SCH$_2$—, —CH$_2$S—, —CF$_2$O—, —OCF$_2$—, —CH=CH—, —CF=CF—, —CH=CF—, —(CH$_2$)$_4$—, —CH=CH—COO—, —OCO—CH=CH—, —OOC—CHR$^{00}$—OOC—, —COO—CHR$^{00}$—COO—, —C≡C— or a single bond,
R$^{00}$ is straight chain or branched alkyl or alkoxy with 1–8 C atoms or phenyl that is optionally mono- or polysubstituted by L,
m is 0, 1 or 2,
R is H, halogen, NO$_2$, CN, SCN, SF$_5$, straight chain branched or cyclic alkyl with 1–25 C atoms wherein one or more CH$_2$ groups can also be replaced by —O—, —S—, —CO—, —NR$^0$—, —CH=CH—, —C≡C— in such a manner that O and/or S atoms are not linked directly to one another, and wherein one or more H-atoms can also be by F or Cl or phenyl that is optionally mono- or polysubstituted by L, or is P-(Sp-X)$_n$—,
P is a polymerizable group,
Sp is a spacer group with 1–20 C atoms,
X has one of the meanings of Z, and
n is 0 or 1.

* * * * *

UNITED STATES PATENT AND TRADEMARK OFFICE
CERTIFICATE OF CORRECTION

PATENT NO. : 6,849,203 B2
DATED : February 1, 2005
INVENTOR(S) : Farrand et al.

It is certified that error appears in the above-identified patent and that said Letters Patent is hereby corrected as shown below:

<u>Title page,</u>
Item [75], Inventors, "Davyhulme" should read -- Manchester --.

<u>Column 24,</u>
Line 35, "-C≡-C-" should read -- -C≡C- --.

<u>Column 27,</u>
Line 19, "-C≡-C-" should read -- -C≡C- --.

<u>Column 31,</u>
Line 28, "wherein R° H" should read -- wherein R° is H --.

<u>Column 32,</u>
Line 53, "37, the polymer" should read -- 37, wherein the polymer --.

<u>Column 33,</u>
Line 10, delete "B independent of A, is an aromatic or alicyclic group with 4-2 C-atoms," and insert the following:
-- A and B   are independently of each other an aromatic or alicyclic group with 4-12 C-atoms,
Z            is in each case independently -O-, -S-, -CO-, -COO-, -OCO-, -CO-NR$^0$-, -NR$^0$-CO-, -CH$_2$CH$_2$-, -CF$_2$CF$_2$-, -OCH$_2$-, -CH$_2$O-, -SCH$_2$-, -CH$_2$S-, CF$_2$O-, -OCF$_2$-, -CH=CH-, -CF=CF-, -CH=CF, -(CH$_2$)$_4$-, -CH=CH-COO-, -OCO-CH=CH-, -OOC-CHR$^{00}$-OOC-, -COO-CHR$^{00}$-COO-, -C≡C- or a single bond,
m            is 0, 1 or 2, --.
Line 25, "R° is H or alkyl with 1-4 C atoms," should be deleted.
Line 28, "has one of the meanings of Z" should read -- is in each independently -O-, -S-, -CO-, -COO-, -OCO, -CO-NR$^0$-, -NR$^0$-CO-, -CH$_2$CH$_2$-, -CF$_2$CF$_2$-, -OCH$_2$-, -CH$_2$O-, -SCH$_2$-, -CH$_2$S-, -CF$_2$O-, -OCF$_2$-, -CH=CH-, -CF=CF-, -CH=CF-, -(CH$_2$)$_4$-, -CH=CH-COO-, -OCO-CH=CH-, -OOC-CHR$^{00}$-OOC-, -COO-CHR$^{00}$-COO-, -C≡C- or a single bond, --.

UNITED STATES PATENT AND TRADEMARK OFFICE
CERTIFICATE OF CORRECTION

PATENT NO. : 6,849,203 B2
DATED : February 1, 2005
INVENTOR(S) : Farrand et al.

It is certified that error appears in the above-identified patent and that said Letters Patent is hereby corrected as shown below:

Column 36,
Line 36, "-$CH_2CF_2$," should read -- -$CH_2CF_2$-, --.

Column 38,
Line 20, "also be by F" should read -- also be replaced by F --.

Signed and Sealed this

Thirty-first Day of May, 2005

JON W. DUDAS
*Director of the United States Patent and Trademark Office*